United States Patent [19]
Timmers et al.

[11] Patent Number: 5,972,822
[45] Date of Patent: Oct. 26, 1999

[54] BISCYCLOPENTADIENYLDIENE COMPLEX CONTAINING ADDITION POLYMERIZATION CATALYSTS

[75] Inventors: Francis J. Timmers; David D. Devore, both of Midland, Mich.; James C. Stevens, Richmond, Tex.

[73] Assignee: The Dow Chemical Company, Midland, Mich.

[21] Appl. No.: 08/474,224

[22] Filed: Jun. 7, 1995

Related U.S. Application Data

[60] Division of application No. 08/481,791, Jun. 7, 1995, which is a continuation-in-part of application No. 08/284,925, Aug. 2, 1994, abandoned.

[51] Int. Cl.$^6$ ............... B01J 31/00; B01J 37/00; C08F 4/02; C08F 4/60

[52] U.S. Cl. ............ 502/103; 526/160; 556/53; 502/117; 502/118; 502/132; 502/152; 502/123; 502/124

[58] Field of Search ............... 556/53; 502/102, 502/103, 117, 152, 118, 132

[56] References Cited

U.S. PATENT DOCUMENTS

| | | | |
|---|---|---|---|
| 3,242,099 | 3/1966 | Manyik et al. | 252/429 |
| 4,808,561 | 2/1989 | Welborn, Jr. | 502/104 |
| 4,912,075 | 3/1990 | Chang | 502/107 |
| 4,914,253 | 4/1990 | Chang | 585/523 |
| 5,008,228 | 4/1991 | Chang | 502/111 |
| 5,064,802 | 11/1991 | Stevens et al. | 502/155 |
| 5,084,534 | 1/1992 | Welborn, Jr. et al. | 526/160 |
| 5,086,025 | 2/1992 | Chang | 502/117 |
| 5,153,157 | 10/1992 | Hlatky et al. | 502/117 |
| 5,198,401 | 3/1993 | Turner et al. | 502/155 |
| 5,321,106 | 6/1994 | LaPointe | 502/152 |
| 5,350,723 | 9/1994 | Neithamer et al. | 502/104 |
| 5,372,682 | 12/1994 | Devore et al. | 556/53 |
| 5,374,696 | 12/1994 | Rosen et al. | 526/126 |
| 5,407,884 | 4/1995 | Turner et al. | 556/53 |
| 5,470,993 | 11/1995 | Devore et al. | 502/103 |
| 5,486,632 | 1/1996 | Devore et al. | 502/117 |
| 5,527,929 | 6/1996 | Timmers et al. | 502/152 |

FOREIGN PATENT DOCUMENTS

| | | |
|---|---|---|
| 0277003 | 8/1988 | European Pat. Off. . |
| 0468651 | 1/1992 | European Pat. Off. . |
| 0520732 | 12/1992 | European Pat. Off. . |
| 0 687 682 | 12/1995 | European Pat. Off. . |
| 8802009 | 3/1988 | WIPO . |
| 9400500 | 1/1994 | WIPO . |

OTHER PUBLICATIONS

*Organometallic Synthesis*, vol. 3, R. Bruce King, et al., pp. 32–34, "(s–CIS–) and (s–trans–$\eta^4$–Butadiene)Zirconocene" (1986).

H. Yasuda et al., Angew. Chem. Int. Ed. Engl., vol. 26, pp. 723–742, 1987.
G. Erker et al., Chem. Ber., vol. 115, pp. 3300–3310, 1982.
H. Yasuda et al., Chem. Lett., pp. 719–722, 1980.
*Organometallics*, "1,3–Diene Complexes of Zirconium and Hafnium Prepared by the Reaction of Enediylmagnesium with $MCl_2Cp_2$." Yasuda, et al., 1982, 1, pp. 388–396.
*Acc. Chem. Res.*, "Unique Chemical Behavior and Bonding of Early–Transition–Metal–Diene Complexes" Yasuda, et al., 1985, 18, pp. 120–126.
*Advances in Organometallic Chemistry*, "The Remarkable Features of ($n^4$–Conjugated Diene) Zirconocene and—hafnocene Complexes" Erker, et al., 1985, vol. 24, pp. 1–39.
*Agnew. Chem. Int. Ed. Engl.*, "($n^3$–Allyl)($n^4$–butadiene)($n^5$–cyclopentadienyl)–Zirconium, a System of Isomeric Monocylopentadienylzirconium(II) Compounds" Erker et al., 1984, vol. 23, pp. 455–456.
*Organometallics*, "Structural Features in Electron–Deficient (n–Pentamethylcyclopentadienyl) titanium–Diene Complexes and Their Catalysis in the Selective Oligomerization of Conjugated Dienes" Yamamoto, et al., 1989, 8, pp. 105–119.
*Chem. Ber.*, "Seven–Membered Heterodimetallic Ring Systems from (Conjugated Diene) Group 4 Metallocene Complexes and Organoaluminium Reagents" Erker et al., 1994, 127, pp. 805–811.
*J.A. Chem. Soc.*, "Syndiospecific Propylene Polymerizations with Group 4 Metallocenes" Ewen, et al., 1988, 110, pp. 6255–6256.
*J. of Organometallic Chem.*, "Synthesis and Molecular Structures of Chiral ansa–Titanocene Derivatives with Bridged Tetrahydroindenyl Ligands" Wild, et al., 1982, 232, pp. 233–247.
*Organometallics*, "The Influence of Aromatic Substituents" Spaleck et al., 1994, 13, pp. 954–963.
*X–Ray Structure Determination*, (The Macmillan Company) Stout, et al., Chapter 19, pp. 430–432.
*Organometallics*, "Structural and Chemical Features of Early Transition–Metal Compounds: Notable Differences between Corresponding Pairs of (s–cis–$n^4$–Conjugated diene)zirconocene and–hafnocene Complexes" Kruger, et al., 1985, 4, pp. 215–223.
J. March, Advanced Organic Chemistry, 4th Ed., Wiley, New York., 1992, 182–184.

*Primary Examiner*—Glenn A. Caldarola
*Assistant Examiner*—J. Pasterczyk

[57] ABSTRACT

Catalysts for polymerizing olefins, diolefins and/or acetylenically unsaturated monomers comprising biscyclopentadienyl, Group 4 transition metal complexes formed with conjugated dienes wherein the diene is bound to the transition metal either in the form of a σ-complex or a π-complex in combination with a cocatalyst or subjected to bulk electrolysis in the presence of compatible, inert non-coordinating anions.

21 Claims, No Drawings

BISCYCLOPENTADIENYLDIENE COMPLEX CONTAINING ADDITION POLYMERIZATION CATALYSTS

CROSS-REFERENCE TO RELATED APPLICATION

This is a division of the application titled BISCYCLOPENTADIENYL DIENE COMPLEXES by Francis J. Timmers, David D. Devore, James C. Stevens, Robert K. Rosen, Jason Patton, and David Neithamer, U.S. Ser. No. 08/481,791, pending, filed Jun. 7, 1995, which is a continuation-in-part of application Ser. No. 08/284,925 filed Aug. 2, 1994, now abandoned.

BACKGROUND OF THE INVENTION

This invention relates to certain biscyclopentadienyl Group 4 transition metal complexes possessing diene ligands and to polymerization catalysts obtained from such. In one form this invention relates to biscyclopentadienyl and substituted bis(cyclopentadienyl)titanium, zirconium or hafnium complexes possessing diene ligands in which the metal is either in the +2 or +4 formal oxidation state which can be activated to form catalysts for the polymerization of olefins and to methods for preparing such complexes and catalysts.

The preparation and characterization of certain biscyclopentadienyl ($Cp_2$) zirconium and hafnium diene complexes is described in the following references: Yasuda, et al., *Organometallics*, 1982, 1, 388 (Yasuda I); Yasuda, et al. *Acc. Chem. Res.*, 1985, 18 120 (Yasuda II); Erker, et al., *Adv. Organomet. Chem.*, 1985, 24, 1 (Erker I); Erker et al. *Chem. Ber.*, 1994, 127, 805 (Erker II); and U.S. Pat. No. 5,198,401. The last reference describes the use of $Cp_2Zr$(diene) where the Zr is in the +4 formal oxidation state as an olefin polymerization catalyst in combination with ammonium borate cocatalysts.

Biscyclopentadienyl Group 4 transition metal complexes in which the metal is in the +4 formal oxidation state, and olefin polymerization catalysts formed from such complexes by combination with an activating agent, e.g., alumoxane or ammonium borate, are known in the art. Thus, U.S. Pat. No. 3,242,099 describes the formation of olefin polymerization catalysts by the combination of biscyclopentadienyl metal dihalides with alumoxane. U.S. Pat. No. 5,198,401 discloses tetravalent biscyclopentadienyl Group 4 transition metal complexes and olefin polymerization catalysts obtained by converting such complexes into cationic form in combination with a non-coordinating anion. Particularly preferred catalysts are obtained by the combination of ammonium borate salts with the biscyclopentadienyl titanium, zirconium or hafnium complexes. Among the many suitable complexes disclosed are bis(cyclopentadienyl)zirconium complexes containing a diene ligand attached to the transition metal through σ-bonds where the transition metal is in its highest (+4) formal oxidation state.

Copending applications, Ser. No. 08/082,197 filed Jun. 24, 1993, (now abandoned) Ser. No. 08/230,051 filed Apr. 19, 1994 (now abandoned) and Ser. No. 08/241,523 filed May 12, 1994 (now U.S. Pat. No. 5,470,993) disclose monocyclopentadienyl diene complexes with titanium or zirconium in which the metal is in the +2 formal oxidation state and the formation of olefin polymerization catalysts from such complexes by the combination of the complex with activator compounds such as alumoxane, ammonium borate salts or strong Lewis acids such as tris(pentafluorophenyl)borane capable of converting the complexes to active forms.

The present invention provides novel olefin polymerization catalysts which can be employed over a wide range of physical conditions and with a wide range of olefin monomers and combinations of such monomers, thus providing an outstanding opportunity of tailor making polyolefins having specifically desired properties.

SUMMARY OF THE INVENTION

The present invention relates to metal complexes containing two cyclopentadienyl groups or substituted cyclopentadienyl groups, said complex corresponding to the formula:

$$CpCp'MD$$

wherein:

M is titanium, zirconium or hafnium in the +2 or +4 formal oxidation state;

Cp and Cp' are each substituted or unsubstituted cyclopentadienyl groups bound in an $\eta^5$ bonding mode to the metal, said substituted cyclopentadienyl group being substituted with from one to five substituents independently selected from the group consisting of hydrocarbyl, silyl, germyl, halo, cyano, hydrocarbyloxy, and mixtures thereof, said substituent having up to 20 nonhydrogen atoms, or optionally, two such substituents (except cyano or halo) together cause Cp or Cp' to have a fused ring structure, or wherein one substituent on Cp and Cp' forms a linking moiety joining Cp and Cp';

D is a stable, conjugated diene, optionally substituted with one or more hydrocarbyl groups, silyl groups, hydrocarbylsilyl groups, silylhydrocarbyl groups, or mixtures thereof, said D having from 4 up to 40 nonhydrogen atoms and forming a π-complex with M when M is in the +2 formal oxidation state, and forming a σ-complex with M when M is in the +4 formal oxidation state. In the diene complexes in which M is in the +2 formal oxidation state, the diene is associated with M as a π-complex in which the diene normally assumes an s-trans configuration or an s-cis configuration in which the bond lengths between M and the four carbon atoms of the conjugated diene are nearly equal (Δd as defined hereafter $\geq -0.15$ Å) whereas in the complexes in which M is in the +4 formal oxidation state, the diene is associated with the transition metal as a σ-complex in which the diene normally assumes a s-cis configuration in which the bond lengths between M and the four carbon atoms of the conjugated diene are significantly different (Δd $<-0.15$ Å). The formation of the complex with M in either the +2 or +4 formal oxidation state depends on the choice of the diene, the specific metal complex and the reaction conditions employed in the preparation of the complex. The complexes wherein the diene is π-bound and M is in the +2 formal oxidation state constitute the preferred complexes of the present invention.

The present invention also relates to novel methods of preparing the CpCp'MD complexes involving the reaction of the biscyclopentadienyl dihydrocarbyl, dihydrocarbyloxy, dihalide or diamide Group 4 metal complexes wherein the metal is in the +4 or +3 formal oxidation state, with a diene, D, and a reducing agent. The use of a reducing agent is optional when starting with biscyclopentadienyl dihydrocarbyl complexes.

Stated more particularly, the diene metal complexes of the present invention may be formed by reacting in any order the following components:

1) a complex of the formula:

$$CpCp'M^*X \text{ or } CpCp'M^{**}X_2$$

wherein;

Cp and Cp' are as previously defined;

M* is titanium, zirconium or hafnium in the +3 formal oxidation state;

M** is titanium, zirconium or hafnium in the +4 formal oxidation state; and

X is a $C_{1-6}$ hydrocarbyl, halide, $C_{1-6}$ hydrocarbyloxy or $diC_{1-6}$ hydrocarbylamide group;

2) a diene corresponding to the formula, D; and
3) optionally when X is $C_{1-6}$ hydrocarbyl, otherwise, not optionally, a reducing agent.

Uniquely, the process when used with diastereomeric mixtures of rac and meso isomers of metallocenes, can result in formation of only the rac diene metal complex.

Further according to the present invention there are provided catalysts for polymerization of addition polymerizable monomers comprising a combination of one or more of the above metal complexes and one or ore activating cocatalysts. The metal complexes wherein the metal is in the +2 formal oxidation state are preferred in the formation of the novel catalysts of this invention.

Finally according to the present invention there is provided a polymerization process comprising contacting one or more addition polymerizable monomers and particularly one or more α-olefins with a catalyst comprising one or more of the above metal complexes and one or more activating cocatalysts.

Generally speaking, the present diene containing complexes are more soluble in hydrocarbon solvents compared to the corresponding dihalide complexes and they are more stable to reductive elimination and other side reactions than are the corresponding dihydrocarbyl complexes. Catalyst systems comprising such diene containing complexes are accordingly better adapted to commercial use than are such alternative systems.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Useful dienes, D, are dienes that do not decompose under reaction conditions used to prepare the complexes of the invention. Under subsequent polymerization conditions, or in the formation of catalytic derivatives of the present complexes, the diene group, D, may undergo chemical reaction or be replaced by another ligand.

The complexes of the present invention wherein M is in the +2 formal oxidation state contain a neutral diene ligand which is coordinated via π-complexation through the diene double bonds, and not through a metallocycle containing σ-bonds. The nature of the diene bond to the metal is readily determined by X-ray crystallography or by NMR spectral characterization according to the techniques of Yasuda I, Yasuda II, and Erker I, supra, as well as the references cited therein. By the term "π-complex" is meant both the donation and back acceptance of electron density by the ligand are accomplished using ligand π-orbitals, i.e., the diene is π-bound (π-bound diene).

Encompassed within the scope of the present invention also are complexes containing a diene ligand which is coordinated formally as a metallocycle containing σ-bonds (σ-bound diene) where the metal is in the +4 formal oxidation state. Such Group 4 metal σ-bound diene complexes have a structure which is formally a metallocyclopentene wherein the bonding between the metal and the diene (depicted as structure i) can be described as a divalent 2-butene-1,4-diyl σ-bonded to a tetravalent metal, optionally containing a single π-bond involving the π electrons between internal carbons of the conjugated diene. Such structures are depicted as structure ii and structure iii as follows:

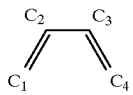

i

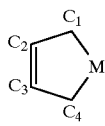

ii

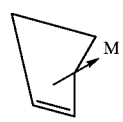

iii

The nomenclature for such σ-bound diene complexes can be either as a metallocyclopentene (referring to the compounds as 2-butene-1,4-diyl compounds) or generically as the parent diene, i.e., butadiene. Those of skill in the art will recognize the interchangability of these names. For example, the prior art biscyclopentadienyl zirconium complex containing a σ-bound 2,3-dimethyl-1,3-butadiene group would be named either bis-cyclopentadienyl 2-butene-2,3-dimethyl-1,4-diyl zirconium or bis-cyclopentadienyl 2,3-dimethyl-1,3-butadiene zirconium.

A suitable method of determining the existence of a π- or σ-complex in conjugated diene containing metal complexes is the measurement of metal-carbon atomic spacings for the four carbons of the conjugated diene using common X-ray crystal analysis techniques. Measurements of atomic spacings between the metal and C1, C2, C3, and C4 (M-C1, M-C2, M-C3, M-C4, respectively) (where C1 and C4 are the terminal carbons of the 4 carbon conjugated diene group and C2 and C3 are the internal carbons of the 4 carbon conjugated diene group) may be made. If the difference between these bond distances, Δd, using the following formula:

$$\Delta d = \left\{ \frac{(M-C1)+(M-C4)}{2} \right\} - \left\{ \frac{(M-C2)+(M-C3)}{2} \right\}$$

is greater than or equal to −0.15 Å, the diene is considered to form a π-complex with M and M is formally in the +2 oxidation state. If Δd is less than −0.15 Å, the diene is considered to form a σ-complex with M and M is formally in the +4 oxidation state.

Examples wherein the above method for determination of π-complexes has been applied to prior art compounds are found in Erker, et al., *Angew. Chem, Int. Ed. Eng.*, 1984, 23, 455–456 (Erker III) and Yamamoto, et al, *Organometallics*, 1989, 8, 105–119. In the former reference $(\eta^3$-allyl)$(\eta^4$-butadiene)$(\eta^5$-cyclopentadienyl)zirconium was crystallographically characterized. The M-C1 and M-C4 distances were both 2.360 (±0.005) Å. The M-C2 and M-C3 distances were both 2.463 (±0.005) Å, giving a Δd of −0.103 Å. In the latter reference $(\eta^5$-pentamethylcyclopentadienyl)$(\eta^4$-1,4-diphenyl-1,3-butadiene)titanium chloride was shown to have M-C1 and M-C4 distances of 2.233 (±0.006) Å. The M-C2 and M-C3 distances were both 2.293 (±0.005) Å, giving a Δd of −0.060 Å. Accordingly, these two complexes contain π-bound diene ligands and the metal of each is in the +2 formal oxidation state. Erker I also disclosed bis (cyclopentadienyl)zirconium (2,3-dimethyl-1,3-butadiene). In this complex the M-C1 and M-C4 distances were 2.300 Å. The M-C2 and M-C3 distances were both 2.597 Å, giving a Δd of −0.297 5<. Accordingly, this complex contains a σ-bound diene and the zirconium is in the +4 formal oxidation state. In the use of such X-ray crystal analysis techniques at least "good" and preferably "excellent" determination quality as defined by G. Stout et al., *X-ray Structure Determination, A Practical Guide,* MacMillan Co., pp. 430–431 (1968) is used.

Alternatively, complexes of the present invention wherein X is a conjugated diene in the form of a π-complex and M is in the +2 formal oxidation state are identified using nuclear magnetic resonance spectroscopy techniques. The teachings of Erker, I to III, supra, C. Krüger, et al. *Organometallics,* 4, 215–223, (1985), and Yasuda I, supra, disclose these well known techniques for distinguishing between π-bound complexes and metallocyclic coordination or σ-bound diene complexes. The teachings of the foregoing references related to π-bound and σ-bound diene complexes is hereby incorporated by reference.

It is to be understood that the present complexes may be formed and utilized as a mixture of the π-complexed and σ-complexed diene compounds where the metal centers are in the +2 or +4 formal oxidation state. Preferably the complex in the +2 formal oxidation state is present in a molar amount from 0.1 to 100.0 percent, more preferably in a molar amount from 10 to 100.0 percent, most preferably in a molar amount from 60 to 100.0 percent. Techniques for separation and purification of the complex in the +2 formal oxidation state from the foregoing mixtures are known in the art and disclosed for example in the previously mentioned Yasuda, I, supra, and Erker, I to III, supra, references and may be employed if desired to prepare and isolate the complexes in greater purity.

The metal complexes used to form the diene complexes of the present invention are the bis(cyclopentadienyl) dihalides, dihydrocarbyls, diamides and dialkoxides which have heretofore been employed in the formation of metallocene complexes, or which are readily prepared using well known synthetic techniques. An extensive list of biscyclopentadienyl complexes is disclosed in U.S. Pat. No. 5,198, 401 which is hereby incorporated by reference.

Preferred complexes of the present invention correspond to the formula:

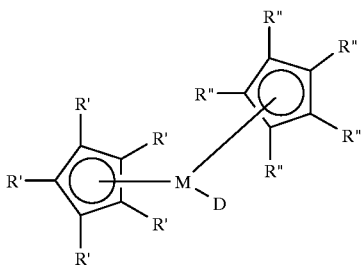

(A)

wherein:

M is titanium, zirconium or hafnium, preferably zirconium or hafnium, in the +2 or +4 formal oxidation state;

R' and R" in each occurrence are independently selected from the group consisting of hydrogen, hydrocarbyl, silyl, germyl, cyano, halo and combinations thereof, said R' and R" having up to 20 non-hydrogen atoms each, or adjacent R' groups and/or adjacent R" groups (when R' and R" are not hydrogen, halo or cyano) together form a divalent derivative (i.e., a hydrocarbadiyl, siladiyl or germadiyl group) or one R' and one R" together (when R' and R" groups are not hydrogen halo or cyano) combine to form a divalent radical (i.e., a hydrocarbadiyl, germadiyl or siladiyl group) linking the two substituted cyclopentadienyl groups; and D is a conjugated diene having from 4 to 30 non-hydrogen atoms, which forms a π-complex with M when M is in the +2 formal oxidation state and a σ-complex with M when M is in the +4 formal oxidation state.

Preferably, R' and R" independently in each ccurrence are selected from the group consisting of ydrogen, methyl, ethyl, and all isomers of propyl, utyl, pentyl and hexyl, as well as cyclopentyl, cyclohexyl, norbornyl, benzyl, and trimethyl silyl, or adjacent R' groups and/or adjacent R" groups on each cyclopentadienyl ring (except hydrogen) are linked together thereby forming a fused ring system such as an indenyl, 2-methyl-4-phenylindenyl, 2-methyl-4-naphthylindenyl, tetrahydroindenyl, fluorenyl, tetrahydrofluorenyl, or octahydrofluorenyl group, or one R' and one R" are linked together forming a 1,2-ethanediyl, 2,2-propanediyl or dimethylsilanediyl linking group.

Examples of suitable D moieties include: $\eta^4$-1,4-diphenyl-1,3-butadiene; $\eta^4$-1,3-pentadiene; $\eta^4$-1-phenyl-1,3-pentadiene; $\eta^4$-1,4-dibenzyl-1,3-butadiene; $\eta^4$-2,4-hexadiene; $\eta^4$-3-methyl-1,3-pentadiene; $\eta^4$-1,4-ditolyl-1,3-butadiene; $\eta^4$-1,4-bis(trimethylsilyl)-1,3-butadiene, 2,3 dimethyl butadiene, isoprene. Of the foregoing 1,4-diphenyl-1,3-butadiene, 1-phenyl-1,3-pentadiene, and 2,4 hexadiene, i.e, the terminally di-$C_{1-10}$ hydrocarbyl substituted 1,3-dienes generally form π-complexes, whereas the solely internally $C_{1-10}$ hydrocarbyl substituted 1,3-dienes, such as isoprene or 2,3-dimethyl butadiene generally form σ-complexes. Preferred dienes are terminally $C_{1-10}$ hydrocarbyl substituted 1,3-butadienes. 2,4-hexadiene, 1-phenyl-1,3-pentadiene, 1,4-diphenylbutadiene or 1,4-ditolylbutadiene Examples of the above metal complexes where the metal is titanium, zirconium or hafnium and preferably zirconium or hafnium include: bis($\eta^5$-cyclopentadienyl)-zirconium s-trans($\eta^4$-1,4-trans, trans-diphenyl-1,3-butadiene), bis (cyclopentadienyl)zirconium s-cis(2,3-dimethyl-1,3-butadiene), (bis-$\eta^5$-cyclopentadienyl)zirconium $\eta^4$-1,4-ditolyl-1,3-butadiene, bis($\eta^5$-cyclopentadienyl)zirconium $\eta^4$-2,4-hexadiene, bis($\eta^5$-cyclopentadienyl)zirconium $\eta^4$-3-methyl-1,3-pentadiene, bis($\eta^5$--cyclopentadienyl)zirconium $\eta^4$-1-phenyl-1,3-pentadiene, bis(pentamethyl-$\eta^5$-cyclopentadienyl)zirconium $\eta^4$-1,4--diphenyl-1,3-butadiene, bis(pentamethyl-$\eta^5$-cyclopentadienyl)zirconium $\eta^4$-1,4-dibenzyl-1,3-butadiene, bis(pentamethyl-$\eta^5$-cyclopentadienyl)zirconium $\eta^4$-2,4-hexadiene, bis(pentamethyl-$\eta^5$-cyclopentadienyl)zirconium $\eta^4$-3-methyl-1,3-pentadiene, bis(ethyltetramethyl-$\eta^5$-cyclopentadienyl) zirconium $\eta^4$-1,4-diphenyl-1,3-butadiene, bis (ethyltetramethyl-$\eta^5$-cyclopentadienyl)-zirconium $\eta^4$-1,4-dibenzyl-1,3-butadiene, bis(ethyltetramethyl-$\eta^5$-cyclopentadienyl)zirconium $\eta^4$-2,4-hexadiene, bis (ethyltetramethyl-$\eta^5$-cyclopentadienyl)zirconium $\eta^4$-3-methyl-1,3-pentadiene, (pentamethyl-$\eta^5$-cyclopentadienyl), ($\eta^5$-cyclopentadienyl)zirconium $\eta^4$-1,4-dibenzyl-1,3-butadiene, (pentamethyl-$\eta^5$-cyclopentadienyl), ($\eta^5$-cyclopentadienyl)zirconium $\eta^4$-2,4-hexadiene, bis(t-butyl-$\eta^5$-cyclopentadienyl)-1,2-zirconium $\eta^4$-1,4-diphenyl-1,3-butadiene, bis(t-butyl-$\eta^5$-cyclopentadienyl)zirconium $\eta^4$-1,4-dibenzyl-1,3-butadiene, bis(t-butyltetramethyl-$\eta^5$-cyclopentadienyl)zirconium $\eta^4$-2,4-hexadiene, $\eta^5$-cyclopentadienyl, (tetramethyl-$\eta^5$-cyclopentadienyl) zirconium $\eta^4$-3-methyl-1,3-pentadiene, bis(pentamethyl-$\eta^5$-cyclopentadienyl)zirconium $\eta^4$-1,4-diphenyl-1,3-butadiene, bis(pentamethyl-$\eta^5$-cyclopentadienyl)zirconium $\eta^4$-1-phenyl-1,3-pentadiene, bis-(tetramethyl-$\eta^5$-cyclopentadienyl)zirconium $\eta^4$-3-methyl-1,3-pentadiene, bis(methyl-$\eta^5$-cyclopentadienyl)zirconium $\eta^4$-1,4-diphenyl-1,3-butadiene, bis($\eta^5$-cyclopentadienyl)zirconium $\eta^4$-1,4-dibenzyl-1,3-butadiene, bis(trimethyl-silyl-$\eta^5$-cyclopetttadienyl)zirconium $\eta^4$-2,4-hexadiene, bis (trimethylsilyl-$\eta^5$-cyclopentadienyl)-zirconium $\eta^4$-3-methyl-1,3--pentadiene, ($\eta^5$-cyclopentadienyl) (trimethylsilyl-$\eta^5$-cyclopentadienyl)zirconium $\eta^4$-1,4- diphenyl-1,3-butadiene, ($\eta^5$-cyclopentadienyl) (trimethylsilyl-$\eta^5$-cyclopentadienyl)zirconium $\eta^4$-1,4-dibenzyl-1,3-butadiene, (trimethylsilyl-$\eta^5$-cyclopentadienyl)-(pentamethyl-$\eta^5$-cyclopentadienyl) zirconium $\eta^4$-2,4-hexadiene, bis(benzyl-$\eta^5$-cyclopentadienyl)zirconium $\eta^4$-3-methyl-1,3-pentadiene, bis($\eta^5$-indenyl)-zirconium $\eta^4$-1,4-diphenyl-1,3-butadiene, bis($\eta^5$-indenyl)zirconium $\eta^4$-1,4-dibenzyl-1,3-butadiene, bis($\eta$5-indenyl)zirconium $\eta^4$-2,4-hexadiene, bis($\eta^5$-indenyl)zirconium $\eta^4$-3-methyl-1,3-pentadiene, bis($\eta^5$-fluorenyl)zirconium $\eta^4$-1,4-diphenyl-1,3-butadiene, (pentamethylcyclopentadienyl)-($\eta^5$-fluorenyl)zirconium $\eta^4$-1-phenyl-1,3-pentadiene, bis($\eta^5$-fluorenyl)zirconium $\eta^4$-1,4-dibenzyl-1,3-butadiene, bis($\eta^5$-fluorenyl)-zirconium $\eta^4$-2,4-hexadiene, and bis($\eta^5$-fluorenyl)zirconium $\eta^4$-3-methyl-1,3-pentadiene.

Additional bis-cyclopentadienyl compounds of formula A include those containing a bridging group linking the cyclopentadienyl groups. Preferred bridging groups are those corresponding to the formula $(ER'''_2)_x$ wherein E is carbon, silicon or germanium, R''' independently each occurrence is hydrogen or a group selected from silyl, hydrocarbyl, hydrocarbyloxy and combinations thereof, or two R''' groups together form a ring system, said R''' having up to 30 carbon or silicon atoms, and x is an integer from 1 to 8. Preferably R''' independently each occurrence is methyl, benzyl, tert-butyl or phenyl.

Examples of the foregoing bridged cyclopentadienyl containing complexes are compounds corresponding to the formula:

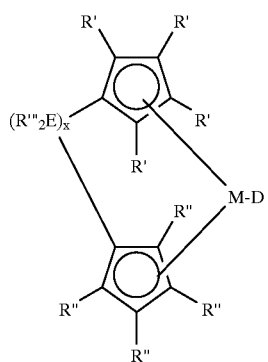

(B)

wherein:

M, D, E, R''' and x are as previously defined, and R' and R'' in each occurrence are independently selected from the group consisting of hydrogen, hydrocarbyl, silyl, germyl, cyano, halo and combinations thereof, said R' and R'' having up to 20 non-hydrogen atoms each, or adjacent R' groups and/or adjacent R'' groups (when R' and R'' are not hydrogen, halo or cyano) together form a divalent derivative (i.e., a hydrocarbadiyl, siladiyl or germadiyl group) or one R' and one R'' together (when R' and R'' groups are not hydrogen halo or cyano) combine to form a divalent radical (i.e., a hydrocarbadiyl, germadiyl or siladiyl group) linking the two cyclopentadienyl groups.

Such bridged structures are especially suited for the preparation of polymers having stereoregular molecular structure. In such capacity it is preferred that the complex be nonsymmetrical or possess a chiral, stereorigid structure. Examples of the first type are compounds possessing different delocalized n-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem,* 232, 233–47, (1982).

Exemplary bridged cyclopentadienyl moieties in the complexes of formula (B) are: dimethylsilanediyl-bis((2-methyl-4-phenyl)-1-indenyl)zirconium s-trans($\eta^4$-1,4-trans-trans-diphenyl-1,3-butadiene), dimethylsilanediyl-bis((2-methyl-4-(1-napthyl))-1-indenyl)zirconium s-trans($\eta^4$-1,4-trans-trans-diphenyl-1,3-butadiene), 1,2-ethanediyl-bis(2-methyl-4-(1-phenyl)-1-indenyl)zirconium s-trans($\eta^4$-1,4-trans-trans-diphenyl-1,3-butadiene), 1,2-ethanediyl-bis(2-methyl-4-(1-napthyl)-1-indenyl)zirconium s-trans($\eta^4$-1,4-trans-trans-diphenyl-1,3-butadiene), [1,2-ethanediylbis(1-indenyl)]zirconium s-trans($\eta^4$-trans,trans-1,4-diphenyl-1,3-butadiene), [1,2-ethanediylbis(1-tetrahydroindenyl)]-zirconium s-trans($\eta^4$-trans,trans-1,4-diphenyl-1,3-butadiene), [1,2-ethanediylbis(1-indenyl)]hafnium s-trans ($\eta^4$-trans,trans-1,4-diphenyl-1,3-butadiene), and [2,2-propanediyl(9-fluorenyl)-(cyclopentadienyl)]-zirconium (trans,trans-1,4-diphenyl-1,3-butadiene).

In general, the complexes of the present invention can be prepared by combining a diene compound, corresponding to the group D in the resulting complex, with a metal complex containing only hydrocarbyl leaving groups. Heating the solution, for example use of boiling toluene, may expedite the reaction. In the event the metal complex contains hydrocarbyloxy, amide or halogen ligands (and otherwise containing the desired structure of the resulting complexes) and optionally when the metal complex contains only hydrocarbyl leaving groups, the metal complex, the diene, or the above mixture of metal complex and diene, is also contacted with a reducing agent. The process preferably is conducted in a suitable noninterfering solvent at a temperature from –100° C. to 300° C., preferably from –78 to 130° C., most preferably from –10 to 120° C. Metal complexes in either the +4 or +3 formal oxidation state may be utilized.

By the term "reducing agent" as used herein is meant a metal or compound which, under reducing conditions can cause the transition metal to be reduced from the +4 or +3 formal oxidation state to the +2 formal oxidation state. The same procedure is employed for the preparation of the diene complexes where M is in the +2 formal oxidation state or in the +4 formal oxidation state, the nature of formal oxidation state of M in the complex being formed being primarily determined by the diene employed. Examples of suitable metal reducing agents are alkali metals, alkaline earth metals, aluminum, zinc and alloys of alkali metals or alkaline earth metals such as sodium/mercury amalgam and sodium/potassium alloy. Specific examples of suitable reducing agent compounds are sodium naphthalenide, potassium graphite, lithium alkyls, aluminum trialkyls and Grignard reagents. Most preferred reducing agents are the alkali metals or alkaline earth metals, $C_{1-6}$ alkyl lithium, tri $C_{1-6}$ alkyl aluminum and Grignard reagents, especially lithium, n-butyl lithium and triethyl aluminum. The use of a $C_{1-6}$ alkyl lithium or triethylaluminum reducing agent is especially preferred.

Highly preferred diene compounds are 1,3-pentadiene; 1,4-diphenyl-1,3-butadiene; 1-phenyl-1,3-pentadiene; 1,4-dibenzyl-1,3-butadiene; 2,4-hexadiene; 3-methyl-1,3-pentadiene; 1,4-ditolyl-1,3-butadiene; and 1,4-bis-(trimethylsilyl)-1,3-butadiene. All geometric isomers of the foregoing diene compounds may be utilized.

Suitable reaction media for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and the like, $C_{1-4}$ dialkyl ethers, $C_{1-4}$ dialkyl ether derivatives of (poly)alkylene glycols, and tetrahydrofuran. Mixtures of the foregoing list of suitable solvents are also suitable.

The recovery procedure involves separation of the resulting byproducts and devolatilization of the reaction medium. Extraction into a secondary solvent may be employed if desired. Alternatively, if the desired product is an insoluble precipitate, filtration or other separation technique may be employed.

The present inventors have further discovered that ansa-rac biscyclopentadienyl Group 4 metal complexes (where "rac" refers to a racemic mixture of enantiomers) uniquely form stable complexes with the conjugated diene, particularly with a trans, trans-terminally disubstituted 1,3-butadiene. The corresponding meso-biscyclopentadienyl Group 4 metal diene complexes are less stable and not recoverable, unless extreme care is utilized. Accordingly, this discovery allows the artisan to separate mixtures of diastereomers of biscyclopentadienyl Group 4 metal complexes containing hydrocarbyl, hydrocarbyloxy, halide or amide leaving groups merely by contacting the mixture with a $C_{4-40}$ conjugated diene and the reducing agent, where called for, and recovering the resulting ansa-rac biscyclopentadienyl Group 4 metal diene complex.

In a further embodiment, the corresponding halide containing complex can be regenerated in the highly pure ansa-rac biscyclopentadienyl form by contacting the ansa-rac biscyclopentadienyl diene complex with an halogenating agent, such as hydrochloric acid or $BCl_3$. Such a process is highly desirable in order to form catalyst components that preferentially form isotactic polymers of prochiral olefins, such as propylene.

Stated in more detail, the foregoing process comprises combining in a solvent in any order:

1) a mixture of rac- and meso-diastereomers of a compound having the formula:

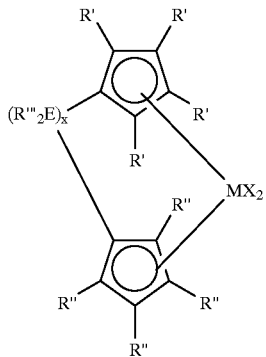

wherein:

M is titanium, zirconium or hafnium;

X is halo, $C_{1-6}$ hydrocarbyl, $C_{1-6}$ hydrocarbyloxy, or di $C_{1-6}$ hydrocarbylamido;

E, R''' and x are as previously defined, and R' and R" in each occurrence are independently selected from the group consisting of hydrogen, hydrocarbyl, silyl, germyl, cyano, halo and combinations thereof, said R' and R" having up to 20 non-hydrogen atoms each, or adjacent R' groups and/or adjacent R" groups (when R' and R" are not hydrogen, halo or cyano) together form a divalent derivative (i.e., a hydrocarbadiyl, siladiyl or germadiyl group) or one R' and one R" together (when R' and R" groups are not hydrogen halo or cyano) combine to form a divalent radical (i.e., a hydrocarbadiyl, germadiyl or siladiyl group) linking the two cyclopentadienyl groups, 2) a $C_{4-40}$ conjugated diene, D, and 3) optionally when X is $C_{1-6}$ hydrocarbyl, otherwise not optionally, a reducing agent;

and recovering the resulting rac-diastereomer of the formula:

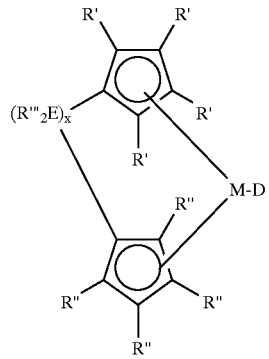

Preferred starting complexes are diastereomeric mixtures of bis(indenyl) metallocenes, corresponding to the formula:

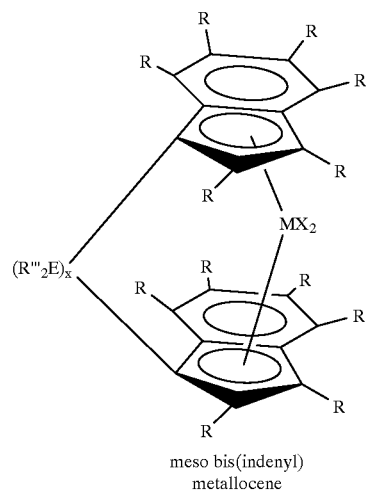

meso bis(indenyl) metallocene or

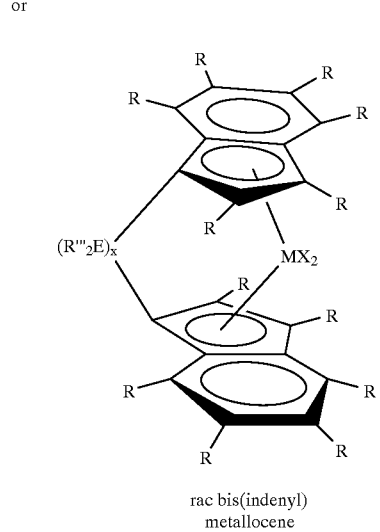

rac bis(indenyl) metallocene or hydrogenated derivatives thereof, wherein,

M, X, E, x, and R''' are as previously defined, and

R in each occurrence is independently selected from the group consisting of hydrogen, hydrocarbyl, silyl, germyl and combinations thereof, said R having up to 20 non-hydrogen atoms each, or adjacent R groups on each separate indenyl system together form a divalent derivative (i.e., a hydrocarbadiyl, siladiyl or germadiyl group) thereby forming a further fused ring. Examples of suitable precursor compounds are found in W. Spaleck, et al., *Organomet.*, 13, 954–963 (1994).

The complexes are rendered catalytically active by combination with one or more activating cocatalysts, by use of an activating technique, or a combination thereof. Suitable activating cocatalysts for use herein include polymeric or oligomeric alumoxanes, especially methylalumoxane, triisobutyl aluminum modified methylalumoxane, or diisobutylalumoxane; strong Lewis acids (the term "strong Lewis acid" as used herein is defined as trihydrocarbyl substituted Group 13 compounds, especially tri(hydrocarbyl)aluminum- or tri(hydrocarbyl)boron compounds and halogenated derivatives thereof, having from 1 to 10 carbons in each hydrocarbyl or halogenated hydrocarbyl group, more especially perfluorinated tri(aryl)boron compounds, and most especially tris(pentafluorophenyl)borane); amine, phosphine, aliphatic alcohol and mercaptan adducts of halogenated tri($C_{1-10}$hydrocarbyl)boron compounds, especially such adducts of perfluorinated tri(aryl)boron compounds; nonpolymeric, ionic, compatible, noncoordinating, activating compounds (including the use of such compounds under oxidizing conditions); bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153, 157, U.S. Pat. No. 5,064,802, EP-A-468,651 (equivalent to U.S. Ser. No. 07/547,718), EP-A-520,732 (equivalent to U.S. Ser. No. 07/876,268), and WO 93/23412 (equivalent to U.S. Ser. No. 07/884,966 filed May 1, 1992) the teachings of which are hereby incorporated by reference.

Combinations of strong Lewis acids, especially the combination of a trialkyl aluminum compound having from 1 to 4 carbons in each alkyl group and a halogenated tri (hydrocarbyl)boron compound having from 1 to 10 carbons in each hydrocarbyl group, especially tris (pentafluorophenyl)borane; further combinations of such strong Lewis acid mixtures with a polymeric or oligomeric alumoxane; and combinations of a single strong Lewis acid, especially tris(pentafluorophenyl)borane with a polymeric or oligomeric alumoxane are especially desirable activating cocatalysts.

When utilizing such strong Lewis acid cocatalysts to polymerize higher α-olefins, especially propylene, to form homopolymers thereof, it has been found especially desirable to also contact the catalyst/cocatalyst mixture with a small quantity of ethylene or hydrogen (preferably at least one mole of ethylene or hydrogen per mole of metal complex, suitably from 1 to 100,000 moles of ethylene or hydrogen per mole of metal complex). This contacting may occur before, after or simultaneously to contacting with the higher α-olefin. If the foregoing Lewis acid activated catalyst compositions are not treated in the foregoing manner, either extremely long induction periods are encountered or no polymerization at all results. The ethylene or hydrogen may be used in a suitably small quantity such that no significant affect on polymer properties is observed. For example, polypropylene having physical properties equal to or superior to polypropylene prepared by use of other metallocene catalyst systems is prepared according to the present invention.

Thus the invention further comprises an activated polymerization catalyst system comprising in combination:
a) a metal complex corresponding to the formula:

wherein:
M, Cp, Cp', and D are as previously defined,
b) a Lewis acid, and
c) ethylene or hydrogen,
the quantity of ethylene or hydrogen being at least equal to the quantity necessary to activate the catalyst system for polymerization of a $C_3$ or higher α-olefin, preferably at least 1 mole per mole of metal complex, more preferably from 1 to 100,000 moles per mole of metal complex.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis, are used such that electrolysis byproducts that would render the metal complex catalytically inactive are not substantially formed during the reaction. More particularly, suitable solvents are materials that are liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (ortho, meta, or para isomers), dimethoxyethane, and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, A⁻. Preferred supporting electrolytes are salts corresponding to the formula $$G^+A^-$$

wherein:

G$^+$ is a cation which is nonreactive towards the starting and resulting complex; and A$^-$ is a noncoordinating, compatible anion.

Examples of cations, G$^+$, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and A$^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis-(perfluoro-aryl) borates having from 1 to 10 carbons in each hydrocarbyl group, especially tetra-n-butylammonium tetrakis(pentafluorophenyl) borate.

Suitable compounds useful as a cocatalyst in one embodiment of the present invention comprise a cation which is a Bronsted acid capable of donating a proton, and an inert, compatible, noncoordinating, anion, A$^-$. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially. Therefore, said single boron atom compounds are preferred.

Preferably such cocatalysts may be represented by the following general formula:

$$(L^*-H)^+_d (A^{d-})$$

wherein:

L$^*$ is a neutral Lewis base;

(L$^*$–H)$^+$ is a Bronsted acid;

A$^{d-}$ is a noncoordinating, compatible anion having a charge of d–, and d is an integer from 1 to 3.

More preferably A$^{d-}$ corresponds to the formula:

$$(M'^{k+}Q_n)^{d-}$$

wherein:

k is an integer from 1 to 3;

n is an integer from 2 to 6;

n–k=d;

M' is an element selected from Group 13 of the Periodic Table of the Elements; and Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide.

In a more preferred embodiment, d is one, i.e. the counter ion has a single negative charge and corresponds to the formula A$^-$. Activating cocatalysts comprising boron which are particularly useful in the preparation of catalysts of this invention may be represented by the following general formula:

$$(L^*-H)^+ (BQ'_4)^-$$

wherein:

L$^*$ is as previously defined;

B is boron in an oxidation state of 3; and

Q' is a fluorinated C$_{1-20}$ hydrocarbyl group.

Most preferably, Q' is in each occurrence a fluorinated aryl group, especially a pentafluorophenyl group.

Illustrative, but not limiting examples of boron compounds which may be used as an activating cocatalyst in the preparation of the improved catalysts of this invention are tri-substituted ammonium salts such as:

trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri (sec-butyl)ammonium tetrakis(pentafluorophenyl) borate, N,N-dimethylanilinium tetrakis(pentafluorophenyl) borate, N,N-diethylanilinium tetrakis(pentafluorophenyl) borate, N,N-dimethyl-(2,4,6-trimethylanilinium) tetrakis (pentafluorophenyl) borate, trimethylammonium tetrakis-(2, 3,4,6-tetrafluorophenylborate, triethylammonium tetrakis-(2,3,4,6-tetrafluorophenyl) borate, tripropylammonium tetrakis-(2,3,4,6-tetrafluorophenyl) borate, tri(n-butyl) ammonium tetrakis-(2,3,4,6-tetrafluorophenyl) borate, dimethyl(t-butyl)ammonium tetrakis-(2,3,4,6-tetrafluorophenyl) borate, N,N-dimethylanilinium tetrakis-(2,3,4,6-tetrafluorophenyl) borate, N,N-diethylanilinium tetrakis-(2,3,4,6-tetrafluorophenyl) borate, and N,N-dimethyl-(2,4,6-trimethylanilinium) tetrakis-(2,3,4,6-tetrafluorophenyl) borate;

dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as: triphenylphosphonium tetrakis(pentafluorophenyl) borate, tri(o-tolyl) phosphonium tetrakis(pentafluorophenyl) borate, and tri(2, 6-dimethylphenyl)phosphonium tetrakis(pentafluorophenyl) borate.

Preferred [L$^*$–H]$^+$ cations are N,N-dimethylanilinium and tributylammonium.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

Ox$^{e+}$ is a cationic oxidizing agent having a charge of e$^+$;

e is an integer from 1 to 3; and

A$^{d-}$, and d are as previously defined.

Examples of cationic oxidizing agents include: ferrocenium, hydrocarbyl-substituted ferrocenium, Ag$^+$, or Pb$^{+2}$. Preferred embodiments of A$^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

©⁺A⁻ wherein:

©⁺ is a $C_{1-20}$ carbenium ion; and

A⁻ is as previously defined. A preferred carbenium ion is the trityl cation, i.e. triphenylcarbenium.

A further suitable ion forming, activating cocatalyst comprises a compound which is a salt of a silylium ion and a noncoordinating, compatible anion represented by the formula:

R#₃Si(X#)ₛ⁺A⁻ wherein:

R# is $C_{1-20}$ hydrocarbyl, s is 0 or 1,

X# is a neutral Lewis base, and

A⁻ is as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443. The use of the above silylium salts as activating cocatalysts for addition polymerization catalysts is claimed in U.S. patent application Ser. No. 08/304,314, filed Sep. 12, 1994.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:1000 to 1:1. In a particularly preferred embodiment of the invention the cocatalyst can be used in combination with a $C_{3-30}$ trihydrocarbyl aluminum compound or oligomeric or polymeric alumoxane. Mixtures of activating cocatalysts may also be employed. It is possible to employ these aluminum compounds for their beneficial ability to scavenge impurities such as oxygen, water, and aldehydes from the polymerization mixture. Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, and methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The combination of the CpCp'MD complexes with strong Lewis acid activating cocatalysts in a preferred embodiment corresponds to one of the two zwitterionic equilibrium structures of the formula:

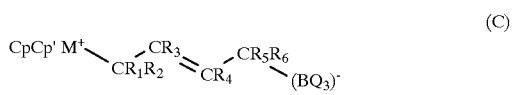

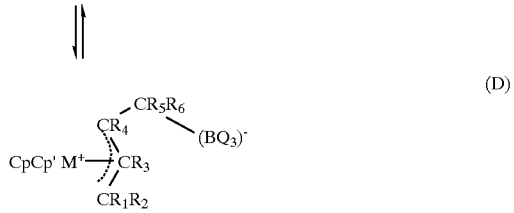

wherein:

M is titanium, zirconium or hafnium in the +4 formal oxidation state;

Cp and Cp' are each substituted or unsubstituted cyclopentadienyl group bound in an $\eta^5$ bonding mode to M, said substituted cyclopentadienyl group being substituted with from one to five substituents independently selected from the group consisting of hydrocarbyl, silyl, germyl, halo, cyano, and mixtures thereof, said substituent having up to 20 nonhydrogen atoms, or optionally, two such substituents other than cyano or halo together cause Cp or Cp' to have a fused ring structure, or one substituent on Cp and Cp' forms a linking moiety joining Cp and Cp';

Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide;

$R_1$, $R_2$, $R_3$, $R_4$, $R_5$ and $R_6$ are independently hydrogen, hydrocarbyl, silyl and combinations thereof, each of said $R_1$ to $R_6$ having up to 20 nonhydrogen atoms; and B is boron in a valence state of 3.

Preferred zwitterionic equilibrium structures correspond to the formula:

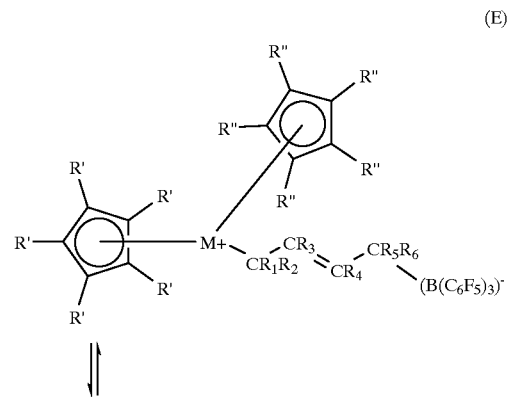

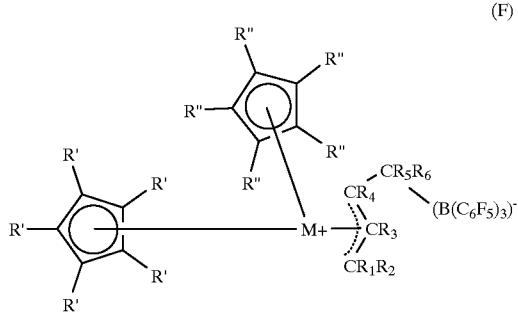

(F)

wherein:
R$_1$, R$_2$, R$_5$ and R$_6$ are hydrogen;
R$_3$ and R$_4$ are hydrogen, C$_{1-4}$ alkyl or phenyl,
M is zirconium in the +4 formal oxidation state, and
R' and R" in each occurrence are independently selected from the group consisting of hydrogen, hydrocarbyl, silyl, germyl, cyano, halo and combinations thereof, said R' and R" having up to 20 non-hydrogen atoms each, or adjacent R' groups and/or adjacent R" groups (when R' and R" are not hydrogen, halo or cyano) together form a divalent derivative (i.e., a hydrocarbadiyl, siladiyl or germadiyl group which forms a fused ring system) or one R' and one R" together (when R' and R" groups are not hydrogen halo or cyano) combine to form a divalent radical (i.e., a hydrocarbadiyl, germadiyl or siladiyl group) linking the two cyclopentadienyl groups.

Most highly preferred are the equilibrium zwitterionic metal coordination complexes corresponding to the formula:

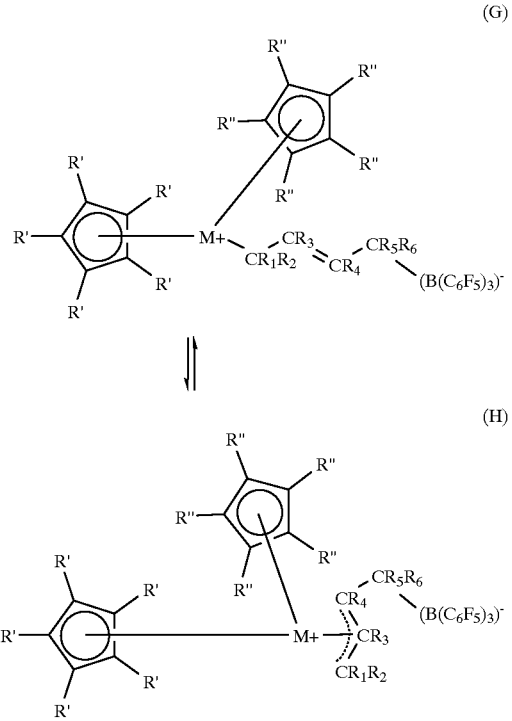

wherein:
M is zirconium in the +4 formal oxidation state;
R$_1$, R$_2$, R$_5$ and R$_6$ are hydrogen;
R$_3$ and R$_4$ are hydrogen or methyl; and
R' and R" in each occurrence are independently selected from the group consisting of hydrogen, hydrocarbyl, silyl, germyl, cyano, halo and combinations thereof, said R' and R" having up to 20 non-hydrogen atoms each, or adjacent R' groups and/or adjacent R" groups (when R' and R" are not hydrogen, halo or cyano) together form a divalent derivative (i.e., a hydrocarbadiyl, siladiyl or germadiyl group which forms a fused ring system) or one R' and one R" together (when R' and R" groups are not hydrogen halo or cyano) combine to form a divalent radical (i.e., a hydrocarbadiyl, germadiyl or siladiyl group) linking the two cyclopentadienyl groups.

The catalysts may be used to polymerize ethylenically and/or acetylenically unsaturated monomers having from 2 to 20 carbon atoms either alone or in combination. Preferred monomers include the C$_{2-10}$ α-olefins especially ethylene, propylene, isobutylene, 1-butene, 1-hexene, 4-methyl-1-pentene, and 1-octene and mixtures thereof. Other preferred monomers include vinylcyclohexene, vinylcyclohexane, styrene, C$_{1-4}$ alkyl substituted styrene, tetrafluoroethylene, vinylbenzocyclobutane, ethylidenenorbornene, piperylene and 1,4-hexadiene.

When the present bridged cyclopentadienyl polymerization catalysts are used to polymerize prochiral olefins, syndiotactic or isotactic polymers are attainable. As used herein, the term "syndiotactic" refers to polymers having a stereoregular structure of greater than 50 percent, preferably greater than 75 percent syndiotactic of a racemic triad as determined by $^{13}$C nuclear magnetic resonance spectroscopy. Conversely, the term "isotactic" refers to polymers having a stereoregular structure of greater than 50 percent, preferably greater than 75 percent isotactic of a meso triad as determined by $^{13}$C nuclear magnetic resonance spectroscopy. Such polymers may be usefully employed in the preparation of articles and objects having an extremely high resistance to deformation due to the effects of temperature via compression molding, injection molding or other suitable technique.

The ethylene/1-olefin copolymers of the present invention are characteristic of the type of ethylene polymers that can be obtained with metallocene catalysts. The polyolefins that can be produced with the catalysts of the present invention range from elastomeric to plastomeric, i.e., substantially non-elastomeric products, depending on the monomers, monomer amounts and polymerization conditions employed. As used herein the term "elastomeric" is meant to signify polymers having tensile modulus values as measured by ASTM D-638 of less than 15,000 N/cm$^2$, preferably less than 5000 N/cm$^2$, and most preferably less than 500 N/cm$^2$. These products find application in all the uses heretofore developed for such polyolefins and can be fabricated into such end-use products by the methods heretofore developed for polyolefins including, for example, molding, casting, extrusion and spinning. The polyolefins obtained with the catalysts of the present invention are useful in such end-use applications as films for packaging, including shrink wrap applications, foams, coating, insulating devices, including for wire and cable, and household items. The polyolefins made with the catalysts of the present invention can be shown to have superior properties in these applications over heretofore used materials in these applications using the tests that have been established to measure performance in the intended end-use or by tests not heretofore applied to measure performance in such end-use applications.

In general, the polymerization may be accomplished at conditions well known in the prior art for Ziegler-Natta or Kaminsky-Sinn type polymerization reactions, i.e., temperatures from 0–250° C. and pressures from atmospheric to 3000 atmospheres. Suspension, solution, slurry, gas phase or high pressure, whether employed in batch or continuous form or under other process conditions, including the recycling of condensed monomers or solvent, may be employed if desired. Examples of such processes are well known in the art for example, WO 88/02009-A1 or U.S. Pat. No. 5,084,534, disclose conditions that can be employed with the polymerization catalysts of the present invention. A support, especially silica, alumina, or a polymer (especially polytetrafluoroethylene or a polyolefin) may be employed, and desirably is employed when the catalysts are used in a gas phase polymerization process. Such supported catalysts are generally not affected by the presence of liquid aliphatic or aromatic hydrocarbons such as may be present under the use of condensation techniques in a gas phase polymerization process. Methods for the preparation of supported catalysts are disclosed in numerous references, examples of which are U.S. Pat. Nos. 4,808,561, 4,912,075, 5,008,228, 4,914,253, and 5,086,025 and are suitable for the preparation of supported catalysts of the present invention.

In most polymerization reactions the molar ratio of catalyst:polymerizable compounds employed is from $10^{-12}:1$ to $10^{-1}:1$, more preferably from $10^{-12}:1$ to $10^{-5}:1$.

Suitable solvents for solution, suspension, slurry or high pressure polymerization processes are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

The catalysts may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770. A more specific process is disclosed in copending application U.S. Ser. No. 08/10958, filed Jan. 29, 1993. The teachings of the foregoing publications and pending applications are hereby incorporated by reference.

Having described the invention the following examples are provided as further illustration thereof and are not to be construed as limiting. Unless stated to the contrary all parts and percentages are expressed on a weight basis.

EXAMPLE 1

Preparation of bis($\eta^5$-cyclopentadienyl)zirconium s-trans ($\eta^4$-1,4-trans, trans-diphenyl-1,3-butadiene)

In an inert atmosphere glove box, 586 mg (2.01 mmol) of $(C_5H_5)_2ZrCl_2$ and 413 mg (2.00 mmol) of trans, trans-1,4-diphenyl-1,3-butadiene are combined in 90 ml of mixed alkanes (Isopar E™, available from Exxon Chemicals Inc.). To the stirred slurry is added 1.60 ml of 2.5M n-butyl lithium. The mixture turns dark red immediately. After stirring at 25° C. for 2 hours, the mixture is heated to reflux for 3 hours. The warm solution is filtered. The red solid residue is extracted with a total volume of 90 ml of warm toluene. The extracts are filtered and combined with the hexanes filtrate. The total volume of the solution is concentrated to 40 ml under reduced pressure. At this point a red precipitate is formed. The mixture is warmed until the solid redissolves and the solution is placed in a freezer (−25° C.). Dark red crystals are subsequently collected on a glass frit. Drying under reduced pressure gives 210 mg (25 percent yield) of $(C_5H_5)_2Zr(\eta^4$-1,4-trans, trans-diphenyl-1,3-butadiene) as verified by $^1$H NMR analysis. The product has a 95 percent s-trans, 5 percent s-cis-configuration.

EXAMPLE 2

Preparation of bis($\eta^5$-cyclopentadienyl)zirconium s-cis(2,3-dimethyl-1,3-butadiene)

In an inert atmosphere glove box, 586 mg (2.01 mmol) of $(C_5H_5)_2ZrCl_2$ and 2.5 ml (22 mmol) of 2,3-dimethyl-1,3-butadiene are combined in 90 ml of mixed alkanes. To the stirred slurry is added 1.60 ml of 2.5M n-butyl lithium. The color changes to red slowly. After stirring for 1 hr at 25° C., the mixture is heated to reflux for ½ hr. The warm solution is then filtered using Celite™ brand diatomaceous earth filter aid available from Fisher Scientific Inc. The filtrate is concentrated to 50 ml and the deep red filtrate placed in the freezer (−25° C.). Dark crystals are collected by filtration and dried under reduced pressure to give 234 mg (39 percent yield) of $(C_5H_5)_2Zr$(2,3-dimethyl-1,3-butadiene) as verified by $^1$H NMR analysis. The product has a s-cis-configuration for the diene.

EXAMPLE 3

Combination of Lewis Acid with bis(cyclopentadienyl) zirconium s-trans($\eta^4$-1,4-trans, trans-diphenyl-1,3-butadiene)

In an inert atmosphere glove box, 8.4 mg (0.020 mmol) of $(C_5H_5)_2Zr$ s-trans($\eta^4$-1,4-trans, trans-diphenyl-1,3-butadiene) of Preparation #1 and 10.0 mg (0.020 mmol) of $B(C_6F_5)_3$ is combined in 0.75 ml of benzene-$d_6$ to form a homogeneous solution. Analysis by $^1$H NMR shows the reactants to be completely consumed.

EXAMPLE 4

Combination of Lewis Acid with bis(cyclopentadienyl) zirconium s-cis(2,3-dimethyl-1,3-butadiene)

In an inert atmosphere glove box, 5.9 mg (0.0195 mmol) of $(C_5H_5)_2Zr$(2,3-dimethyl-1,3-butadiene) and 10.0 mg (0.0195 mmol) of $B(C_6F_5)_3$ is combined in 0.75 ml of benzene-$d_6$ to give a homogeneous solution. $^1$H NMR analysis indicated that the mixture had been cleanly converted to the zwitterionic compound, $(C_5H_5)_2Zr+$ $(CH_2CMe=CMeCH_2B(C_6F_5)_3^-)$ or its $\eta^3$ equivalent isomer. δ ($C_6D_6$), 5.31 (s, 5H), 4.91 (s, 5H), 2.37 (d, 10.5 Hz, 1H), 1.09 (s, 3H), 0.93 (d, 10.5 Hz), −0.3 (broad) and −0.7 ppm (broad).

EXAMPLE 5

Polymerization using a Combination of $(C_5H_5)_2Zr$ s-trans ($\eta^4$-1,4-trans, trans-diphenyl-1,3-butadiene) and $B(C_6F_6)_3$ A two-liter reactor is charged with 746 g of mixed alkanes and 120 g of 1-octene comonomer. Hydrogen is added as a molecular weight control agent by differential pressure expansion from a 75 ml addition tank from 300 psig (2.1) MPa) to 275 psig (1.9 MPa). The reactor is heated to the polymerization temperature of 140° C. and saturated with ethylene at 500 psig (3.4 MPs). 5.00 μmol of the catalyst combination of Example 3 (0.00500M solutions in toluene) is transferred to a catalyst addition tank. The polymerization is initiated by injecting this solution into the contents of the reactor. The polymerization conditions are maintained for 10 minutes with ethylene provided on demand at 500 psi (3.4 MPa). The polymer solution is removed from the reactor and combined with 100 mg of a hindered phenol anti-oxidant (Irganox™ 1010 available from Ciba Geigy Corp.). Volatiles are removed from the polymer in a vacuum oven set at 120° C. for about 20 hours. The polymer yield is 16.8 g.

EXAMPLE 6
Preparation of Ethylene/Propylene Copolymer using [bis(cyclopentadienyl)]zirconium (2,3-dimethyl-1,3-butadiene) and $B(C_6F_5)_3$ A two liter reactor is charged with 656 g of mixed alkanes and 207 g of propylene comonomer. Hydrogen was added by differential pressure expansion from a 75 ml additional tank from 300 psig (2.1 MPa) to 274 psig (1.9 MPa). The reactor is heated to the polymerization temperature of 140° C. and saturated with ethylene at 500 psig (3.4 MPa). 10 μmol of [bis(cyclopentadienyl)]zirconium (2,3-dimethyl-1,3-butadiene) and 10 μmol $B(C_6F_5)_3$ in toluene is transferred to a catalyst addition tank. The polymerization is initiated by injecting this solution into the contents of the reactor. The polymerization conditions are maintained for 20 minutes with ethylene provided on demand at 500 psi (3.4 MPa). The reaction mixture was removed from the reactor and the volatiles were removed in a vacuum oven set at 120° C. for about 20 hours 21.0 g Of an ethylene/propylene copolymer was obtained.

EXAMPLE 7
Combination of $(C_5H_5)_2Zr$ s-trans($\eta^4$-1,4-trans, trans-diphenyl-1,3-butadiene) with Dimethylanilinium Tetrakis(pentafluorophenyl) Borate In an inert atmosphere glove box, 0.043 g (0.010 mmol) of bis-cyclopentadienyl zirconium s-trans($\eta^4$-1,4-trans, trans-diphenyl-1,3-butadiene) is dissolved in 20 ml of toluene followed by addition of 0.0780 g (0.099 mmol) of dimethylanilinium tetrakis(pentafluorophenyl) borate using 10 ml of toluene to wash the solids into the reaction flask. After one hour the solvent is removed under reduced pressure. The product is washed with pentane (3×10 ml with drying after the final wash). The product is isolated as an oil.

EXAMPLE 8
Electrolytic Preparation of [$(C_5H_5)_2Zr$ s-trans($\eta^4$-1,4-trans, trans-diphenyl-1,3-butadiene)] [tetrakis(pentafluorophenyl)borate]

A standard H-cell for electrolysis comprising two electrode wells separated by a fine glass frit, platinum mesh working and counter electrodes, and a silver reference electrode is placed inside an inert atmosphere glove box filled with argon. Each half of the cell is filled with 1,2-difluorobenzene solvent (5 ml in the working compartment, 4 ml in the counter compartment) and tetra-n-butylammonium tetrakis(pentafluorophenyl) borate supporting electrolyte (8 mmol). The complex, bis(cyclopentadienyl)Zr s-trans($\eta^4$-1,4-trans, trans-diphenyl-1,3-butadiene) (0.017 g) is placed in the working compartment. A sweep of the working electrode potential is used to determine the voltage to be applied during electrolysis. The solution is stirred and the potential is stepped to the first oxidation wave of the complex and adjusted to obtain a 1.5 mA current. The applied potential is turned off when the current drops to 30 percent of its original value having passed a total of 3.3 coulombs. This represents a conversion of 72 percent. The working compartment solution is then pipetted into a round bottom flask and the solvent is removed under vacuum. The resulting solid product is extracted with toluene (2.0 ml) and is directly transferred to the polymerization reaction in Example 9.

EXAMPLE 9
Polymerization using Catalyst of Example 8

A 2 L stirred reactor is charged with the desired amounts of mixed alkanes solvent and 15 g 1-octene comonomer. Hydrogen is added as a molecular weight control agent by differential pressure expansion (25 Δpsi (200 ΔkPa)) from an approximately 75 ml addition tank at 300 psi (2.1 MPa). The reactor is heated to the polymerization temperature and saturated with ethylene at 500 psi (3.4) MPa. 5.00 μmol of the catalyst of Example 8 dissolved in toluene is transferred to a catalyst addition tank and injected into the reactor. The polymerization is allowed to proceed for the desired time with ethylene provided on demand at 500 psi (3.4 MPa). After 15 minutes run time, the solution is removed from the reactor and quenched with isopropanol. A hindered phenol anti-oxidant is added to the polymer solution. The resulting solid polymer of ethylene and 1-octene is dried in a vacuum oven set at 120° C. for about 20 hours.

EXAMPLE 10
Polymerization using $(C_5H_5)_2Zr$ s-trans($\eta^4$-1,4-trans, trans-diphenyl-1,3-butadiene) with Alumoxane A stirred 5 L autoclave reactor is charged with 1850 g of anhydrous hexane through a mass-flow meter. A solution containing 100 μmols of triisopropylaluminum modified methylalumoxane (MMAO, obtained from Akzo Corporation) in 10 ml of hexane is then added to the reactor via a pressurized stainless steel cylinder prior to heating to 80° C. At this point the reactor pressure is increased to 10 psig (70 kPa) by the addition of hydrogen followed by ethylene sufficient to bring the total pressure to 175 psig (1.21 Mpa). The ethylene is supplied continuously to the reactor by a demand feed regulator on the line. 12.5 μmol of the diene complex of Example 1 is slurried in hexane and is then added to the reactor to initiate the polymerization. After 30 minutes the ethylene flow is stopped and the reactor is vented and cooled. The resulting polyethylene is filtered and dried at 80° C. overnight in a vacuum oven.

EXAMPLE 11
Preparation of rac-[1,2-ethanediylbis(1-indenyl)]zirconium s-trans-($\eta^4$-1,4-trans,trans-diphenyl-1,3-butadiene)

In an inert atmosphere glove box, 837 mg (2.00 mmol) of rac-[1,2-ethanediylbis(1-indenyl)]zirconium dichloride and 413 mg (2.00 mmol) of trans,trans-1,4-diphenyl-1,3-butadiene were combined in approximately 90 ml mixed alkanes. To this mixture was added 1.60 ml of 2.5M butyl lithium in mixed alkanes (4.00 nmol). This mixture turned dark red immediately. After stirring at ambient temperature for one half hour the mixture was heated to reflux for two and one half hours. The solution was cooled and filtered through Celite™ brand filtration aid. The solid residue was extracted using a total of 100 ml of toluene. The extracts were filtered and the filtrates were combined. The filtrate was concentrated to 20 ml under reduced pressure and the concentrate cooled to 30° C. A red solid was collected on a glass frit. The volatiles were removed from the solid under reduced pressure to give 767 mg of a red crystalline solid. The identity and purity of the compound was confirmed using $^1$H NMR spectroscopy. δ($C_6D_6$), 7.55 (d, 8.8 Hz, 2H), 7.2 (m), 7.3–6.8 (m, 4H), 6.76 (m, 2H), 6.60 (d, 8.5 Hz, 2H), 5.23 (d, 3.3 Hz, 2H), 4.58 (d, 3.3 Hz, 2H), 3.35 (m, 2H), 3.01 (m, 4H) and 1.83 ppm (m, 2H).

EXAMPLE 12
Combination of Lewis Acid with rac-[1,2-ethanediylbis(1-indenyl)]zirconium s-trans($\eta^4$-1,4-trans,trans-diphenyl-1,3-butadiene)

In an inert atmosphere glove box, 9 mg (~0.2 mmol) of rac-[bis-1,2-ethanediylbis(1-indenyl)]zirconium s-trans($\eta^4$-1,4-trans, trans-diphenyl-1,3-butadiene) and 10 mg (0.02 mmol) of $B(C_6F_5)_3$ is combined with 0.75 mL of benzene-$d_6$ to give a homogeneous solution of the complex as established by $^1$H NMR analysis. The dissolved reaction product is useful as a polymerization catalyst for the polymerization of ethylene following the procedure of Example 10.

EXAMPLE 13
Preparation of bis(n-butylcyclopentadienyl)zirconium-s-cis (2,3-dimethyl-1,3-butadiene)

In an inert atmosphere glove box, 2.01 mmol of (n-butyl $C_5H_4)_2ZrCl_2$ and 22 mmol of 2,3-dimethyl-1,3-butadiene are combined in 90 ml of hexane. To the stirred slurry is added 1.60 ml of 2.5M n-butyl lithium. The color changes to red slowly. After stirring for 1 hr at room temperature, the mixture is heated to reflux for ½ hr. The warm solution is then filtered using a diatomaceous earth filter aid. The filtrate is concentrated to 50 ml and the deep red filtrate placed in the freezer (−25° C.). Dark crystals are collected by filtration and dried under reduced pressure to give (n-butyl $C_5H_4$)Zr s-cis(2,3-dimethyl-1,3-butadiene) based on $^1$H NMR analysis.

EXAMPLE 14
Combination of Lewis Acid with bis(n-butylcyclopentadienyl)zirconium s-cis(2,3-dimethyl-1,3-butadiene)

In an inert atmosphere glove box, 0.0195 mmol of (n-butyl $C_5H_4)_2Zr$(2,3-dimethyl-1,3-butadiene) and 0.0195 mmol of $B(C_6F_5)_3$ is combined in 0.75 ml of benzene-$d_6$ to give a homogeneous solution. The conversion to (n-butyl $C_5H_4)_2Zr^+(CH_2CMe=CMeCH_2B(C_6F_5)_3)^-$ or its $\eta^3$ equivalent isomer) is established by $^1$H NMR analysis. The resulting product is useful as a catalyst for the polymerization of ethylene as described in Example 10.

EXAMPLE 15
Preparation of rac[dimethylsilanediylbis(1-(2-methyl-4-phenyl)indenyl)]zirconium (trans,trans-1,4-diphenyl-1,3-butadiene)

In an inert atmosphere glove box, 106.6 mg (0.170 mmol) of rac-[dimethylsilanediylbis(1-(2-methyl-4-phenyl)indenyl)]zirconium dichloride and 35.1 mg (0.170 mmol) of trans,trans-1,4-diphenyl-1,3-butadiene were combined in approximately 50 ml toluene. To this mixture was added 0.14 ml of 2.5M butyl lithium in mixed alkanes (0.35 mmol). After stirring at about 25° C. for two hours the mixture had turned from yellow to orange. The mixture was heated in toluene (about 80° C.) for three hours during which time it had turned dark red. The solution was cooled and filtered through Celite™ brand filter aid. The volatiles were removed from the solid under reduced pressure to give a red solid. This was dissolved in 15 ml mixed alkanes which was then removed under reduced pressure. $^1$H NMR spectroscopy showed the desired n-diene product as well as some butylated material. The solid residue was dissolved in toluene and heated to reflux for five hours. Volatiles were then removed under reduced pressure and the residue dissolved in a small amount of mixed alkanes (ca 10 ml) and the resulting solution was cooled to −30° C. A solid was isolated by decanting the solution from the solid and removing the remaining volatiles from the solid under reduced pressure.

$^1$H NMR spectroscopy showed the desired compound, rac-[dimethylsilanediylbis(1-(2-methyl-4-phenyl)indenyl)] zirconium (trans,trans-1,4-diphenyl-1,3-butadiene) as the major component containing an indenyl type ligand.

EXAMPLE 16
Preparation of Ethylene/Propylene/Diene Terpolymers

A 2 L batch reactor is charged with 500 mL of mixed alkanes, 75 mL of 5-ethylidene-1-norbornene, and 500 mL of liquefied propylene. The reactor is heated to 60° C., and is saturated with ethylene at 500 psig (3.4 MPa). In an inert atmosphere drybox, 10 μmol of a 0.005M solution in toluene of rac-[dimethylsilanediylbis(1-(2-methyl-4-phenyl) indenyl)]zirconium (trans,trans-1,4-diphenyl-1,3-butadiene) and 10 μmol of a 0.005 m solution of $B(C_6F_5)_3$ in toluene are combined and the mixture is transferred to the reactor to initiate polymerization. After 15 minutes, the reactor is vented and the solution is drained from the reactor. The polymer solution is combined with 100 mg of antioxidant and the volatiles are removed under reduced pressure in order to isolate the rubbery terpolymer of ethylene/propylene/ethylidene norbornene.

EXAMPLE 17
Preparation of Ethylene/Propylene/7-methyl-1,6-Octadiene Copolymer The procedure in Example 16 is substantially followed except that 75 mL of 7-methyl-1,6-octadiene is used in place of the ethylidene norbornene. After removal of the solvent, a rubbery terpolymer of ethylene/propylene/7-methyl-1,6-octadiene is obtained.

EXAMPLE 18
Preparation of Ethylene/Propylene/Piperylene Copolymer

The procedure in Example 16 is substantially followed except that 75 mL of piperylene (1,3-pentadiene) is used in place of the ethylidene norbornene. After removal of the solvent, a rubbery terpolymer of ethylene/propylene/piperylene is obtained.

EXAMPLE 19
Preparation of Isotactic Polypropylene

A two liter reactor is charged with 500 mL of mixed alkanes, and 500 mL of liquefied propylene. Ethylene (10 μmol) is added to the reactor. The reactor is heated to 60° C., and 10 μmol of the combination of rac-1,2-[bis-(1-indenyl) ethanediyl]zirconium s-trans($\eta^4$-1,4-trans-trans-diphenyl-1, 3-butadiene) with $B(C_6F_5)_3$ of Example 12 (0.005M solution in toluene) is added slowly in order to control the exothermic polymerization. After 15 minutes polymerization at 60° C., the reactor is vented and the reactor contents are removed. The solvent is removed under vacuum and crystalline, solid isotactic polypropylene is isolated.

EXAMPLE 20
Preparation of 2,2-propanediyl(cyclopentadienyl-9-fluorenyl)zirconium(2,3-dimethyl-1,3-butadiene)

In an inert atmosphere glovebox, 5.0 g of 2,2-propanediyl (cyclopentadienyl-9-fluorenyl)zirconium dichloride (11.56 mmol) and 0.95 g of (2,3-dimethyl-1,3-butadiene) (11.56 mmol) (available from Boulder Scientific Inc.) are combined in 500 mL of toluene. This mixture is stirred and 9.3 mL of 2.5M n-butyl lithium is added. After stirring for 2 hours at room temperature, the mixture is filtered through a fritted funnel. Toluene is added to the fritted funnel and the solids are extracted. The total volume of the filtrate is concentrated under reduced pressure to obtain the product in crude form. The crude product can be purified by recrystallization in order to obtain a higher purity product.

EXAMPLE 21

Preparation of Syndiotactic Polypropylene

A two liter reactor is charged with 500 mL of mixed alkanes, and 500 mL of liquefied propylene. A small quantity of ethylene (0.001 weight percent based on propylene) is added to the reactor. The reactor is heated to 60° C. In an inert atmosphere drybox, 10 μmol of the 2,2-propanediyl (cyclopentadienyl-9-fluorenyl)zirconium(2,3-dimethyl-1,3-butadiene) (0.005M solution in toluene) is combined with 10 μmoles of $B(C_6F_5)_3$ (0.005M solution in toluene). This mixture is added slowly to the reactor in order to control the exothermic polymerization. After 15 minutes polymerization at 60° C., the reactor is vented and the reactor contents are removed. The solvent is removed under vacuum and crystalline, solid syndiotactic polypropylene is isolated.

EXAMPLE 22

Preparation of Syndiotactic Polypropylene

The procedure of Example 21 is substantially followed, except that no ethylene is added to the reactor and the catalyst mixture is 10 μmol of 2,2-propanediyl (cyclopentadienyl-9-fluorenyl)zirconium(2,3-dimethyl-1,3-butadiene) (0.005M solution in toluene) combined with 10 mmoles of methylaluminoxane (MAO) (1.0M solution in toluene). This mixture is added slowly to the reactor in order to control the exothermic polymerization. After 15 minutes polymerization at 60° C., the reactor is vented and the reactor contents are removed. The solvent is removed under reduced pressure and crystalline, solid syndiotactic polypropylene is isolated.

EXAMPLE 23

Preparation of Supported Catalysts (a) Preparation of support

Dried silica (2.5 g, Davison 948, dried at 800° C.) is slurried with 10 mL of 1.0M methylaluminoxane (MAO, 1.0M in toluene) and the mixture is stirred for 30 minutes. The slurry is filtered and washed five times with 10 mL portions of pentane. The washed slurry is dried under vacuum.

(b) Preparation of supported catalyst

Bis(n-butylcyclopentadienyl)zirconium s-trans($\eta^4$-1,4-trans-trans-diphenyl-1,3-butadiene) is prepared analogously to bis(cyclopentadienyl)zirconium s-trans($\eta^4$-1,4-trans-trans-diphenyl-1,3-butadiene) (Example 1). A 100 mL flask is charged with 0.50 g of bis(n-butylcyclopentadienyl)zirconium s-trans($\eta^4$-1,4-trans-trans-diphenyl-1,3-butadiene) (1.17 mmol). A solution of MAO (50 mL of a 1.0M solution in toluene) is added. The solution is stirred for five minutes followed by the addition of 2.5 g of the treated silica obtained from part (a) above. The mixture is stirred for five minutes, and the toluene is removed under vacuum to give the supported catalyst.

EXAMPLE 24

Slurry Polymerization using Supported Catalyst

A 1 L reactor is charged with 400 mL of hexane, and 0.2 mL of triethylaluminum (1.6M in heptane). The reactor is heated to 80° C. and ethylene is provided on demand at 100 psig (0.7 MPa). After the reactor is saturated with ethylene, 0.5 g of the prepared supported catalyst obtained from step (b) above is added to initiate the polymerization. After 60 minutes, the reaction is stopped by venting the reactor and the solid polyethylene is recovered.

EXAMPLE 25

Preparation of rac-dimethylsilyl-bis(2-methyl-4-(1-napthyl)-1-indenyl)zirconium s-trans-($\eta^4$-1,4-trans-trans-diphenyl-1,3-butadiene)

In an inert atmosphere glovebox, 5.0 g of rac-dimethylsilyl-bis(2-methyl-4-(1-napthyl)-1-indenyl)-zirconium dichloride (6.84 mmol) and 1.408 g of trans, trans-1,4-diphenyl-1,3-butadiene (6.84 mmol) are combined in 500 mL of toluene. This mixture is stirred and 5.5 mL of 2.5M n-butyl lithium is added. After stirring for 2 hours at room temperature, the mixture is heated to reflux for 3 hours. The warm solution is filtered through a fritted funnel. Warm toluene is added to the fritted funnel and the solids are extracted. The total volume of the filtrate is concentrated under reduced pressure to obtain the product in crude form. The crude product can be purified by recrystallization in order to obtain a higher purity product.

EXAMPLE 26

Polymerization using Supported Catalyst

Silica (2.5 g, Davison™ 952, available from Davison Catalyst Corp.) is dried at 600° C. To this dried silica is added 25 mL of toluene in an inert atmosphere drybox. The slurry is stirred while 0.50 g of rac-dimethylsilyl-bis(2-methyl-4-napthyl-1-indenyl)-zirconium ($\eta^4$-1,4-trans-trans-diphenyl-1,3-butadiene) is added. After 10 minutes, the solvent is removed under reduced pressure to give a supported catalyst. A 2 L reactor is charged with 500 mL of mixed alkanes and 500 mL of liquefied propylene, and 5 mL of 1M methylaluminoxane (MAO) in toluene is added. The reactor is heated to 60° C. To the reactor is added 0.50 g of the silica supported catalyst to initiate the polymerization. After 30 minutes, the reactor is vented and the high melting, crystalline polypropylene is recovered.

EXAMPLE 27

Polymerization using Unsupported Catalyst

A 2 L reactor is charged with 500 mL of mixed alkanes, 500 mL of liquefied propylene, and 0.2 mL of triethylaluminum (1.6M in heptane) is added. The reactor is heated to 60° C. A small quantity of ethylene (0.001 weight percent based on propylene) is added to the reactor. In an inert atmosphere drybox, 10 μmole of bis(2-methyl-4-napthyl-1-indenyl)zirconium ($\eta^4$-1,4-trans-trans-diphenyl-1,3-butadiene) (0.005M in toluene) is combined with 10 μmoles of $B(C_6F_5)_3$ (0.005M solution in toluene). This mixture is added slowly to the reactor in order to control the exothermic polymerization. After 15 minutes polymerization at 60° C., the reactor is vented and the reactor contents are removed. The solvent is removed under vacuum and crystalline, solid isotactic polypropylene is isolated.

EXAMPLE 28

Polymerization with N,N-dimethylanilinium Tetrakis (pentafluorophenyl)borate Activating Cocatalyst The procedure of Example 27 is substantially repeated except that 10 μmoles of a 0.005M toluene solution of N,N-dimethylanilinium tetrakis(pentafluorophenyl)borate is used in place of the $B(C_6F_5)_3$ cocatalyst. After 15 minutes polymerization at 60° C., the reactor is vented and the reactor contents are removed. The solvent is removed under vacuum and crystalline, solid isotactic polypropylene is isolated.

EXAMPLE 29

High-Pressure Polymerization

A 1000 mL stirred steel autoclave equipped to perform Ziegler polymerizations at pressures up to 250 MPa and temperatures up to 300° C. is used. The reaction system is equipped with a thermocouple and a pressure transducer to measure temperature and pressure continuously, and with means to supply purified ethylene, nitrogen, hydrogen, and 1-butene. The reactor is also equipped with means for continuously introducing a measured flow of catalyst solution and equipment for rapidly venting and quenching the reaction and for collecting the polymer product. The catalyst is prepared by combining 564 mg of bis(n-butyl-cyclopentadienyl)zirconium s-trans($\eta^4$-1,4-trans-trans-diphenyl-1,3-butadiene) with 1.0 L of 0.8M MAO in 10 L of toluene in an inert atmosphere drybox. This catalyst solution is continuously fed into the reactor at a rate necessary to maintain a temperature of 180° C. in the reactor. During the run, ethylene and 1-hexene are pressured into the reactor at a total pressure of 100 MPa at a mass flow of 50 kg/hr. The reactor is stirred at 1000 rpm. A solid copolymer of ethylene and 1-hexene is obtained.

EXAMPLE 30
High Pressure Polymerization

The procedure of Example 29 is repeated, except that no MAO is used and the catalyst is prepared by simultaneously adding equimolar amounts of 0.005M solutions of bis(n-butylcyclopentadienyl)zirconium s-trans($\eta^4$-1,4-trans-trans-diphenyl-1,3-butadiene) and $B(C_6F_5)_3$ to the flowing stream of 1-hexene just prior to the reactor. A solid copolymer of ethylene and 1-hexene is obtained.

EXAMPLE 31
Preparation of rac-[1,2-ethanediylbis(1-indenyl)]zirconium s-trans($\eta^4$-trans,trans-1,4-diphenyl-1,3-butadiene) from a Mixture of rac and meso [1,2-ethanediylbis(1-indenyl)] zirconium Dichlorides In an inert atmosphere glove box, 418.5 mg (1.00 mmol) of [1,2-ethanediylbis(1-indenyl)]zirconium dichloride (95 percent rac, 5 percent meso by $^1$H NMR analysis) and 207 mg (1.00 nmol) of trans,trans-1,4-diphenyl-1,3-butadiene were combined in approximately. 70 ml mixed alkanes. To this mixture was added 0.80 ml of 2.5M butyl lithium in mixed alkanes (2.00 mmol). This mixture turned dark red immediately. After stirring at about 25° C. for one half hour the mixture was heated to reflux for three hours. The solution was cooled and filtered through Celite™ brand filter aid and the mixed alkanes filtrate set aside. The solid residue was extracted twice with 30 ml toluene, the extracts were filtered and the filtrates combined. The filtrate was concentrated to 15 ml under reduced pressure and the concentrate cooled to −30° C. A red solid was collected on a glass frit. The volatiles were removed from the solid under reduced pressure to give 200 mg of a red crystalline solid. The identity and purity of the compound was confirmed using $^1$H NMR spectroscopy and it was found not to contain any meso isomer. The toluene filtrate was combined with the mixed alkanes filtrate and the volatiles were removed under reduced pressure. The solid was washed briefly with −30° C. pentane. Drying under reduced pressure gave a red powder. $^1$H NMR analysis showed the product was rac-[1,2-ethanediylbis(1-indenyl)]zirconium (trans,trans-1,4-diphenyl-1,3-butadiene) contaminated with some free diene but with no meso product.

EXAMPLE 32
Preparation of rac-[1,2-ethanediylbis(1-indenyl)]zirconium dichloride from rac-[1,2-ethanediylbis(1-indenyl)] zirconium (trans,trans-1,4-diphenyl-1,3-butadiene) and HCl A concentrated solution of rac-[1,2-ethanediylbis(1-indenyl)]zirconium (trans,trans-1,4-diphenyl-1,3-butadiene) was prepared in $C_6D_6$ and the $^1$H NMR spectrum obtained. To this deep red solution was added 0.1 ml of 12M aqueous HCl. The mixture turned bright yellow quickly and yellow microcrystals formed on the walls of the sample tube. $^1$H NMR analysis showed the sample was rac-[1,2-ethanediylbis(1-indenyl)]zirconium dichloride with no meso isomer present. The solvent was decanted from the yellow crystals which were then washed with 0.75 ml of $CDCl_3$ which was also decanted from the remaining solid. $C_6D_6$ was added to the solid and the $^1$H NMR spectrum obtained. The spectrum showed the material to be rac-[1,2-ethanediylbis(1-indenyl)]zirconium dichloride with most of the organic fragments absent.

EXAMPLE 33
Preparation of rac-[1,2-ethanediylbis(1-tetrahydroindenyl)] zirconium (trans,trans-1,4-diphenyl-1,3-butadiene)

In an inert atmosphere glove box, 213 mg (0.500 mmol) of rac-[1,2-ethanediylbis(1-tetrahydroindenyl)]-zirconium dichloride and 103 mg (0.500 mmol) of trans,trans-1,4-diphenyl-1,3-butadiene were combined in about 35 ml mixed alkanes. To this mixture was added 0.40 ml of 2.5M butyl lithium in mixed alkanes (1.0 mmol). This mixture turned dark red gradually. After stirring at about 25° C. for one half hour the mixture was heated to reflux for one half hour. The solution was cooled and filtered through Celite™ brand filter aid. The residue was washed three times each with 10 mL of mixed alkanes. The solid residue was extracted with toluene (five times with 12 ml each), the extracts were filtered and the filtrates combined. Volatiles were removed from the filtrate under reduced pressure to give 98.0 mg of a red crystalline solid. The identity and purity of the compound was confirmed using $^1$H NMR spectroscopy. δ ($C_6D_6$), 7.50 (d, 7.7 Hz, 4H), 7.29 (m, 4H), 7.02 (t, 7.4 Hz, 1H), 4.70 (d, 3 Hz, 2H), 4.26 (d, 3 Hz, 2H), 3.57 (m, 2H), 3.15 (m, 2H), 2.8 (m, 2H), 2.5 (m), 2.0 (m), 1.8 (m) and 1.4 ppm (m).

EXAMPLE 34
Preparation of rac-[1,2-ethanediylbis(1-indenyl)]hafnium (trans,trans-1,4-diphenyl-1,3-butadiene)

In an inert atmosphere glove box, 505.7 mg (1.00 mmol) of rac-[1,2-ethanediylbis(1-indenyl)]hafnium dichloride and 206.3 mg (1.00 mmol) of trans,trans-1,4-diphenyl-1,3-butadiene were combined in about 70 ml mixed alkanes. To this mixture was added 0.80 ml of 2.5M butyl lithium in mixed alkanes (2.0 mmol). This mixture turned dark orange gradually. After stirring at about 25° C. for five hours the mixture was filtered through Celite™ brand filter aid and the filtrate was concentrated under reduced pressure to an orange powder. $^1$H NMR analysis in $C_6D_6$ showed the solid to be a mixture of the dibutyl hafnium complex and free diene. The solid was dissolved in 50 ml of toluene and heated to reflux for two hours during which time the solution became dark red. The volatiles were removed under reduced pressure. The solid residue was washed with mixed alkanes. The solid was dried under reduced pressure to give 217 mg of a red powder. The product was identified using $^1$H NMR spectroscopy, δ ($C_6D_6$), 7.50 (d, 9.6 Hz, 2H), 7.28 (m), 7.19, 6.98 (m), 6.74 (m), 6.60 (d, 8.5 Hz), 5.17 (d, 3 Hz, 2H) 4.68 (d, 3 Hz, 2H), 3.36 (m, 2H), 2.96 (m) and 1.70 ppm (m, 2H).

EXAMPLE 35
Preparation of [2,2-propanediyl(1-fluorenyl) (cyclopentadienyl)]zirconium (trans,trans-1,4-diphenyl-1,3-butadiene)

In an inert atmosphere glove box, 433 mg (1.00 mmol) of [2,2-propanediyl(1-fluorenyl)(cyclopentadienyl)]zirconium dichloride (previously recrystallized from boiling toluene) and 206 mg (1.00 mmol) of trans,trans-1,4-diphenyl-1,3-butadiene were combined in about 60 ml toluene. To this mixture was added 0.80 ml of 2.5M butyl lithium in mixed alkanes (2.0 mmol). This mixture turned dark red immediately. After stirring at ambient temperature for one half hour the mixture was filtered through Celite™ brand filter aid. The filtrate was concentrated to 15 ml under reduced pressure and cooled to −30° C. A crystalline dark purple solid was collected on a glass frit and the solid was washed once with cold mixed alkanes to give 226 mg of solid. The identity and purity of the compound was confirmed using $^1$H NMR spectroscopy. δ ($C_6D_6$), 7.4 (d), 7.25 (m), 7.0 (m), 6.85 (m), 6.6 (d), 6.55 (m), 5.6 (s), 5.1 (s) 4.3 (m), 1.6 (s) and 1.2 ppm (m).

Batch Solution Polymerization Procedure Examples 36–49

All solvents and liquid monomers are sparged with nitrogen and, together with any gases used, are passed through activated alumina prior to use. A two liter reactor is charged with mixed alkanes solvent and optionally 1-octene or styrene comonomer. Propylene monomer, if used, is measured using a MicroMotion™ brand gas flow rate meter which gives total monomer supplied. Hydrogen, if desired, is added by differential pressure expansion from a 75 ml addition tank from 300 psig (2070 Kpa) to a lower pressure, usually 275 psig (1890 Kpa). Batch quantities of ethylene are then added using the flow meter. If ethylene monomer is used on demand, the reactor contents are first heated to within 5° C. of the polymerization temperature and saturated with ethylene typically at 500 psig (3450 Kpa). The catalyst and cocatalyst are combined in toluene and transferred to a catalyst addition tank. When the reactor contents are at the desired run temperature, the polymerization is initiated by injecting the catalyst solution into the contents of the reactor. The polymerization temperature is maintained by external resistive heating and internal cooling for the desired run time. The pressure is maintained at 500 psig (3450 Kpa) if ethylene is provided on demand. Occasionally, additional catalyst and cocatalyst solution is added to the contents of the reactor in the foregoing manner. After the desired run time has elapsed, the contents of the reactor are removed and combined with hindered phenol antioxidant solution. Polymer is isolated by removing the volatile components from the reaction mixture in a vacuum oven set at from 120 to 130° C. for about 20 hours.

EXAMPLE 36
Preparation of Isotactic Polypropylene using rac-[1,2-ethanediylbis(1-indenyl)]zirconium (trans,trans-1,4-diphenyl-1,3-butadiene) and $B(C_6F_5)_3$ The general procedure was followed using 719 g mixed alkanes, 26 Δpsi (170 kPa) hydrogen, 200 g propylene monomer with a temperature of 70° C. and a polymerization time of 60 minutes. The catalyst was prepared by combining 2 μmol rac-[1,2-ethanediylbis(1-indenyl)]zirconium (trans, trans-1,4-diphenyl-1,3-butadiene) and 2 μmol $B(C_6F_5)_3$ in toluene. The yield of isotactic polypropylene was 181.5 g, (74 percent m pentad by $^{13}$C NMR analysis).

EXAMPLE 37
Preparation of Isotactic Polypropylene using rac-[1,2-ethanediylbis(1-indenyl)]zirconium (trans,trans-1,4-diphenyl-1,3-butadiene) and $B(C_6F_5)_3$ with Ethylene The polymerization conditions of Example 36 were substantially repeated excepting that a small quantity of ethylene was added to the reactor contents initially instead of hydrogen. Quantities of ingredients used were 723 g solvent, 3 g ethylene, 200 g propylene monomer with a polymerization temperature of 70° C. and a run time of 30 minutes. The catalyst was prepared by combining 2 μmol rac-[1,2-ethanediylbis(1-indenyl)]zirconium (trans,trans-1,4-diphenyl-1,3-butadiene) and 2 μmol $B(C_6F_5)_3$ in toluene. 94.2 g of isotactic polypropylene/ethylene copolymer was obtained (73 percent m pentad by $^{13}$C NMR analysis).

EXAMPLE 38
Preparation of Isotactic Polypropylene using rac-[1,2-ethanediylbis(1-indenyl)]zirconium (trans,trans-1,4-diphenyl-1,3-butadiene) and N,N-dimethylanilinium tetrakis(pentafluorophenyl)borate, $[Me_2NHPh]^+[B(C_6F_5)_4]^-$ The general procedure was followed using 715 g mixed alkanes, 25 Δpsi (170 kPa) hydrogen, 200 g propylene monomer, a polymerization temperature of 70° C. and a polymerization time of 67 minutes. The catalyst was prepared by combining 4 μmol rac-[1,2-ethanediylbis(1-indenyl)]zirconium (trans,trans-1,4-diphenyl-1,3-butadiene) and 4 μmol $[Me_2NHPh]^+[B(C_6F_5)_4]^-$ in toluene. 164.8 g of crystalline polypropylene was obtained.

EXAMPLE 39
Preparation of Ethylene/Propylene Copolymer Polymerization using rac-[1,2-ethanediylbis(1-tetrahydroindenyl)]zirconium (trans,trans-1,4-diphenyl-1,3-butadiene) and $B(C_6F_5)_3$ The general procedure was followed using 840 g mixed alkanes, 32 Δpsi (220 kPa) hydrogen, 75 g propylene monomer and ethylene monomer on demand at 500 psig (3450 kPa) with a temperature of 130° C. and run time of 15 minutes. The catalyst was prepared by combining 3 μmol rac-[1,2-ethanediylbis(1-tetrahydroindenyl)]zirconium (trans,trans-1,4-diphenyl-1,3-butadiene) and 3 μmol $B(C_6F_5)_3$ in toluene. 19.6 g of an ethylene/propylene copolymer was obtained.

EXAMPLE 40
Preparation of Isotactic Polypropylene using rac-[1,2-ethanediylbis(1-(2-methyl-4-phenyl)indenyl)]zirconium (trans,trans-1,4-diphenyl-1,3-butadiene) and $B(C_6F_5)_3$ with Hydrogen The general procedure was followed (except as noted below) using 723 g solvent, 100 Δpsi (690 kPa) hydrogen, 201 g propylene monomer with a temperature of 70° C. and a polymerization time of 30 minutes. The catalyst was prepared by combining 2 μmol rac-[1,2-ethanediylbis(1-(2-methyl-4-phenyl)indenyl)]zirconium (trans,trans-1,4-diphenyl-1,3-butadiene) and 2 μmol $B(C_6F_5)_3$ in toluene. The reactor bottom valve plugged and the contents of the reactor could not be emptied immediately after the polymerization. The reactor was vented. The reactor was then pressurized with nitrogen gas to 400 psig (2.8 MPa) and vented. This was repeated two more times to remove the unreacted propylene monomer. The contents of the reactor were then heated quickly to 160° C. and the contents removed as a solution. 107.2 g of isotactic polypropylene was obtained (57 percent m pentad by $^{13}$C NMR analysis).

EXAMPLE 41
Preparation of Ethylene/Propylene Copolymer using [2,2-propanediyl(9-fluorenyl)(cyclopentadienyl)]zirconium (trans,trans-1,4-diphenyl-1,3-butadiene) and $B(C_6F_5)_3$ The general procedure was followed using 719 g mixed alkanes, 25 Δpsi (170 kPa) hydrogen, 200 g propylene monomer and 26 g ethylene monomer with a temperature of 70° C. and polymerization time of 30 minutes. The catalyst was prepared by combining 10 μmol [2,2-propanediyl(1-fluorenyl)(cyclopentadienyl)]zirconium (trans,trans-1,4-diphenyl-1,3-butadiene) and 10 μmol $B(C_6F_5)_3$ in toluene. 69.4 g Of an ethylene/propylene amorphous copolymer was obtained.

EXAMPLE 42
Preparation of Syndiotactic Polypropylene using [2,2-propanediyl(1-fluorenyl)(cyclopentadienyl)]zirconium (trans,trans-1,4-diphenyl-1,3-butadiene) and methylalumoxane (MAO)

The general procedure was followed using 719 g mixed alkanes, 25 Δpsi (170 kPa) hydrogen, 200 g propylene monomer and 26 g ethylene monomer with a temperature of 70° C. and run time of 30 minutes. The catalyst was prepared by combining 10 μmol [2,2-propanediyl(1-fluorenyl)(cyclopentadienyl)]zirconium (trans,trans-1,4-diphenyl-1,3-butadiene) and 10,000 μmol 10 percent MAO in toluene. 35.0 g Of syndiotactic polypropylene was obtained (74.7 percent r pentad by $^{13}C$ NMR analysis).

EXAMPLE 43
Preparation of Isotactic Polypropylene using rac-[1,2-ethanediylbis(1-indenyl)]hafnium (trans,trans-1,4-diphenyl-1,3-butadiene) and $B(C_6F_5)_3$ The general procedure was followed using 715 g mixed alkanes, 25 Δpsi (170 kPa) hydrogen, 200 g propylene monomer with a temperature of 70° C. and polymerization time of 60 minutes. The catalyst was prepared by combining 5 μmol rac-[1,2-ethanediylbis(1-indenyl)]hafnium (trans, trans-1,4-diphenyl-1,3-butadiene) and 5 μmol $B(C_6F_5)_3$ in toluene. 60.7 g Of isotactic polypropylene was obtained (83 percent m pentad by $^{13}C$ NMR analysis).

Gas Phase Reactor Description

Gas phase reactions were carried out in a 6-liter gas phase fluid bed reactor having a four inch diameter, thirty inch long, cylindrical fluidization zone and an eight inch diameter ten inch long velocity reduction zone which are connected by a transition section having tapered walls. Monomers, hydrogen and nitrogen enter the bottom of the reactor where they pass through a gas distributor plate. The flow of gas is typically 2 to 8 times the minimum fluidization velocity of the solid particles. Most of the suspended solids disengage in the velocity reduction zone. The reactant gases exit the top of the fluidization zone and pass through a dust filter to remove any particulates. The gases then pass through a gas booster pump. No condensation of volatiles is employed. The polymer is allowed to accumulate in the reactor over the course of the reaction. Polymer is removed from the reactor to a recovery vessel by opening a valve located at the bottom of the fluidization zone. The polymer recovery vessel is kept at a lower pressure than the reactor.

EXAMPLE 44
Preparation Ethylene/1-butene Copolymer Under Gas Phase Polymerization Conditions The catalyst was prepared by impregnating a toluene solution of 2 μmol rac-[1,2-ethanediylbis(1-indenyl)] zirconium (trans,trans-1,4-diphenylbutadiene) and 6 μmol $B(C_6F_5)_3$ on 0.1 grams of Davison™ 948 silica (available from Davison Chemical Company) which had been treated with 1.0 gram of triethylaluminum/gram of silica. The reactor was charged with 240 psi (1650 kPa) of ethylene, 5.4 psi (37 kPa) of 1-butene, 1.3 psi (9 kPa) of hydrogen and 53 psi (370 kPa) of nitrogen. The reactor temperature was set at 72° C. and the catalyst was injected. A 6° C. exotherm was recorded upon catalyst injection. The temperature returned to 74° C. within 3 minutes and the temperature remained steady at 74° C. for the duration of the run. 14.3 g of a free-flowing polymer powder were recovered after 39 minutes operation.

EXAMPLE 45
Preparation Ethylene/Propylene Copolymer having Isotactic Propylene Segments The catalyst was prepared by impregnating a toluene solution of 2 μmol rac-[1,2-ethanediylbis(1-indenyl)] zirconium (trans,trans-1,4-diphenylbutadiene) and 6 μmol $B(C_6F_5)_3$ on 0.1 grams of Davison™ 948 silica (available from Davison Chemical Company) which had been treated with 1.0 gram of triethylaluminum/gram of silica. The reactor was charged with 95 psi (650 kPa) of propylene, about 3 psi (20 kPa) of ethylene, 1.5 psi (10 kPa) of hydrogen and 42 psi (290 kPa) of nitrogen. The reactor temperature was set at 70° C. and the catalyst was injected. The temperature remained steady at 70° C. for the duration of the polymerization. 4.6 g Of a free-flowing isotactic propylene/ethylene copolymer powder were recovered after 60 minutes. (m pentad=71 percent by $^{13}C$ NMR analysis).

EXAMPLE 46
Preparation of rac-1,2-ethanediyl[bis-(1-indenyl)]zirconium ($\eta^4$-1-phenyl-1,3-pentadiene)

In an inert atmosphere glove box 0.896 g (2.14 mmol) of rac-1,2-ethanediyl[bis-(1-indenyl)]zirconium dichloride (in 50 ml of toluene) were combined with 0.309 g of 1-phenyl-1,3-pentadiene (2.14 mmol), followed by addition of 1.8 ml of nBuLi (4.5 mmol, in hexane). The color of the reaction quickly turned red. The reaction mixture was stirred at about 25° C. for 30 minutes followed by heating at reflux for two hours, followed by continued stirring at about 25° C. for 18 hours. The product was collected by filtering, concentrating the filtrate to approximately 30 ml, and cooling the filtrate to approximately −34° C. for about 18 hours. 0.225 g (21.4 Percent) of recrystallized product was isolated as dark red microcrystals after decanting the mother liquor and drying the product under reduced pressure. The product was identified by $^1H$ NMR spectrum as rac-1,2-ethanediyl[bis-(1-indenyl)]zirconium($\eta^4$-1-phenyl-1,3-pentadiene).

EXAMPLE 47
Batch Isotactic Polypropylene Polymerization Using rac-[bis-1,1'-($\eta^5$-indenyl)-1,2-ethanediyl]zirconium ($\eta^4$-1-phenyl-1,3-pentadiene) and $B(C_6F_5)_3$ with Hydrogen The general polymerization procedure was followed using 734 g solvent, 26 Δpsi (180 kPa) hydrogen, 200 g propylene monomer with a reaction temperature of 70° C. and run time of 30 minutes. The catalyst was prepared by combining 4 μmol rac-[bis-1,1'-($\eta^5$-indenyl)-1,2-ethanediyl]zirconium ($\eta^4$-1-phenyl-1,3-pentadiene) and 4 μmol $B(C_6F_5)_3$ in toluene. 82 g of crystalline polypropylene was obtained.

EXAMPLE 48
Batch Ethylene/Styrene Polymerization using rac-[1,2-ethanediylbis-(1-indenyl)]zirconium ($\eta^4$-s-trans-1,4-trans,trans-diphenyl-1,3-butadiene) and $B(C_6F_5)_3$ with Hydrogen The general polymerization procedure was followed using 365 g solvent, 51 Δpsi (350 kPa) hydrogen, 458 g styrene monomer with a temperature of 70° C. and 200 psig (1.4 MPa) of ethylene on demand and a run time of 15 minutes. The catalyst was prepared by combining 4 μmol of rac-1,2-ethanediyl[bis-(1-indenyl)]zirconium ($\eta^4$-s-trans-1,4-trans,trans-diphenyl-1,3-butadiene) and 4 μmol of $B(C_6F_5)_3$ in toluene. 19.8 g of an ethylene/styrene copolymer was isolated.

EXAMPLE 49

Batch Ethylene/1-Octene Polymerization using rac-[1,2-ethanediylbis-(2-methyl-4-phenyl-1-indenyl)]zirconium ($\eta^4$-s-trans-1,4-trans,trans-diphenyl-1,3-butadiene) and $B(C_6F_5)_3$ with Hydrogen The general procedure was followed using 741 g solvent, 26 $\Delta$psi (180 kPa) hydrogen, 129 g 1-octene monomer with a temperature of 140° C. and 500 psig (3.4 MPa) of ethylene on demand and run time of 15 minutes. The catalyst was prepared by combining 1 $\mu$mol of rac-[1,2-ethanediylbis-(2-methyl-4-phenyl-1-indenyl)]zirconium ($\eta^4$-s-trans-1,4-trans,trans-diphenyl-1,3-butadiene) and 1 $\mu$mol $B(C_6F_5)_3$ in toluene. 13.1 g of an ethylene/1-octene copolymer was isolated.

What is claimed is:

1. Compositions of matter useful as olefin polymerization catalysts comprising:

1) a metal complex containing two cyclopentadienyl groups or substituted cyclopentadienyl groups, said complex corresponding to the formula:

CpCp'MD wherein:

M is titanium, zirconium or hafnium in the +2 or +4 formal oxidation state;

Cp and Cp' are each substituted or unsubstituted cyclopentadienyl groups bound in an $\eta^5$ bonding mode to the metal, said substituted cyclopentadienyl group being substituted with from one to five substituents independently selected from the group consisting of hydrocarbyl, silyl, germyl, halo, cyano, hydrocarbyloxy, and mixtures thereof, said substituent having up to 20 nonhydrogen atoms, or optionally, two such substituents (except cyano or halo) together cause Cp or Cp' to have a fused ring structure, or wherein one substituent on Cp and Cp' forms a linking moiety joining Cp and Cp';

D is a stable, conjugated diene, optionally substituted with one or more hydrocarbyl groups, silyl groups, hydrocarbylsilyl groups, silylhydrocarbyl groups, or mixtures thereof, said D having from 4 up to 40 nonhydrogen atoms and forming a $\pi$-complex with M when M is in the +2 formal oxidation state, and forming a $\sigma$-complex with M when M is in the +4 formal oxidation state;

2) a cocatalyst or activating technique selected from the group consisting of:

2a) Lewis acids selected from the group consisting of $C_{1-30}$ hydrocarbyl substituted Group 13 compounds; halogenated $C_{1-30}$ hydrocarbyl substituted Group 13 compounds; amine-, phosphine-, aliphatic alcohol-, and mercaptan- adducts of halogenated $C_{1-30}$ hydrocarbyl substituted Group 13 compounds, and combinations thereof;

2b) oxidizing salts corresponding to the formula:

$(Ox^{e+})_d(A^{d-})_e$ wherein:

$Ox^{e+}$ is a cationic oxidizing agent having a charge of e+;

e is 1 or 2; and

A is a noncoordinating compatible anion having a charge of d−;

d is an integer from 1 to 3;

2c) carbenium salts corresponding to the formula:

©$^+$A$^-$ wherein:

©$^+$ is a $C_1$–$C_{20}$ carbenium ion; and

A$^-$ is a noncoordinating compatible anion having a charge of −1;

2d) an activating technique comprising electrolyzing the metal complex under bulk electrolysis conditions in the presence of an electrolyte of the general formula:

G$^+$A$^-$ wherein

A− is a noncoordinating compatible anion having a charge of −1; and

G+ is a cation which is non-reactive towards the metal complex and the catalyst;

2e) polymeric or oligomeric alumoxanes;

2f) salts of a silylium ion and a noncoordinating, compatible anion represented by the formula:

$R^{\#}_3Si(X^{\#})_s{}^+A^-$ wherein:

$R^{\#}$ is $C_{1-20}$ hydrocarbyl, s is 0 or 1, $X^{\#}$ is a neutral Lewis base, and A$^-$ is as previously defined; and 2g) Bronsted acid salts having the formula:

$(L-H)^+{}_d(A)^{d-}$ wherein:

L is a neutral Lewis base;

$(L-H)^+$ is the conjugate Bronsted acid of L;

A is a noncoordinating compatible anion having a charge of d−; and d is an integer from 1 to 3;

with the proviso that when the cocatalyst is a Bronsted acid salt of 2g), then:

D is a terminally $C_{1-10}$ hydrocarbyl substituted 1,3-butadiene $\pi$-bonded to the M; and M is titanium, zirconium or hafnium in the +2 formal oxidation state.

2. The composition of matter of claim 1 wherein the metal complex corresponds to the formula:

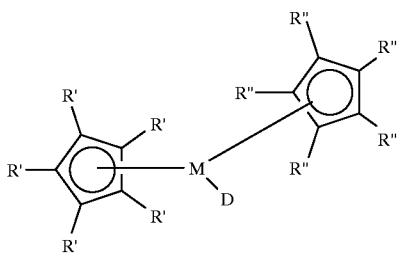

wherein:
M is zirconium or hafnium, in the +2 or +4 formal oxidation state;
R' and R" in each occurrence are independently selected from the group consisting of hydrogen, hydrocarbyl, silyl, germyl, cyano, halo and combinations thereof, said R' and R" having up to 20 non-hydrogen atoms each, or adjacent R' groups or adjacent R" groups (when R' and R" are not hydrogen, halo or cyano) together form a divalent derivative thereby forming a fused ring, or one R' and one R" together (when R' and R" groups are not hydrogen halo or cyano) combine to form a divalent radical linking the two substituted cyclopentadienyl groups; and
D is as previously defined in claim 1.

3. The composition of claim 1 wherein the metal complex is:
a 1,2-ethanediyl(bis-,$\eta^5$-indenyl)zirconium diene complex,
a 1,2-ethanediylbis(4-phenyl-1-indenyl)zirconium diene complex,
a 1,2-ethanediyl bis(2-methyl-4-phenyl-1-indenyl) zirconium diene complex,
a 1,2-ethanediyl bis(4-naphthyl-1-indenyl)zirconium diene complex,
a 1,2-ethanediyl bis(2-methyl-4-naphthyl-1-indenyl) zirconium diene complex,
a 1,2-ethanediyl bis(2-methyl-4,7-diphenyl-1-indenyl) zirconium diene complex,
a 2,2-propanediyl bis($\eta^5$-indenyl)zirconium diene complex,
a 2-(cyclopentadienyl)-2-(9-fluorenyl) propanediylzirconium diene complex,
a 2,2-propanediyl bis(4-phenyl-1-indenyl)zirconium diene complex,
a 2,2-propanediyl bis(2-methyl-4-phenyl-1-indenyl) zirconium diene complex,
a 2,2-propanediyl bis(4-naphthyl-1-indenyl)zirconium diene complex,
a 2,2-propanediylbis(2-methyl-4,7-diphenyl-1-indenyl) zirconium diene complex,
a dimethylsilanediylbis(2-methyl-4-naphthyl-1-indenyl) zirconium diene complex,
a dimethylsilanediylbis($\eta^5$-indenyl)zirconium diene complex,
a dimethylsilanediyl(cyclopentadienyl)(9-fluorenyl) zirconium diene complex,
a dimethylsilanediyl bis(4-phenyl-1-indenyl)zirconium diene complex,
a dimethylsilanediyl bis(2-methyl-4-phenyl-1-indenyl) zirconium diene complex,
a dimethylsilanediyl bis(4-naphthyl-1-indenyl)zirconium diene complex, or
a dimethylsilanediyl bis(2-methyl-4,7-diphenyl-1-indenyl)zirconium diene complex.

4. The composition of claim 1 wherein the Lewis acid is tris(pentafluorophenyl)borane.

5. The composition of claim 4 additionally comprising a polymeric or oligomeric alumoxane.

6. The composition of claim 1 additionally comprising hydrogen or ethylene.

7. The composition of claim 2, wherein M is zirconium or hafnium in the +2 formal oxidation state and the diene is bound to the metal in a π-complex structure.

8. The composition of claim 7 wherein D is a 1,3-butadiene that is terminally substituted with one or two $C_{1-10}$ hydrocarbyl groups.

9. The composition of claim 7, wherein the diene is 1,4-diphenylbutadiene or 1,4-ditolylbutadiene.

10. The composition of claim 7, 8 or 9 wherein the cocatalyst is tris(pentafluorophenyl)borane.

11. The composition of claim 10, additionally comprising a polymeric or oligomeric alumoxane.

12. The composition of claim 2, wherein M is zirconium or hafnium in the +4 formal oxidation state and the diene is bound to the metal in a σ-complex structure and is in the s-cis configuration.

13. The composition of claim 12 wherein D is 1,3-butadiene or a 1,3-butadiene substituted at the 2 or 3 position with one or two $C_{1-10}$ hydrocarbyl groups.

14. The composition of claim 13, wherein the diene is isoprene or 2,3-dimethylbutadiene.

15. The composition of claim 12, 13, or 14, wherein the cocatalyst is tris(pentafluorophenyl)borane.

16. The composition of claim 15, additionally comprising a polymeric or oligomeric alumoxane.

17. The composition of claim 1 obtained by combining a diene complex with a Bronsted acid salt wherein the diene complex has the formula:

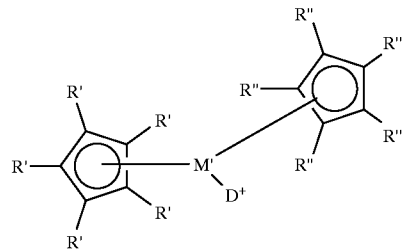

wherein:
M' is zirconium or hafnium in the +2 formal oxidation state;
R' and R" in each occurrence is independently selected from the group consisting of hydrogen, hydrocarbyl, silyl, germyl, cyano, halo and combinations thereof, said R' and R" having up to 20 non-hydrogen atoms, or adjacent R' groups or adjacent R" groups (when R' and R" are not hydrogen, halo or cyano) together form a divalent derivative thereby forming a fused ring or where one R' and one R" combine to form a divalent radical linking the two cyclopentadienyl groups;
D is a $C_{1-10}$ hydrocarbyl substituted 1,3-butadiene which is π-bonded to the metal; and
the Bronsted acid salt has the formula:

$(L-H)^+(BQ'_4)^-$ wherein:

L is a neutral Lewis base;

(L–H)⁺ is the conjugate Bronsted Acid of L;

B is boron;

Q' is a fluorinated $C_1$ to $C_{20}$ hydrocarbyl group.

18. The composition of claim 17 wherein $(BQ'_4)^-$ is tetrakispentafluorophenyl borate, M' is zirconium or hafnium and the diene is 2,4-hexadiene, 1-phenyl-1,3-pentadiene, 1,4-diphenylbutadiene or 1,4-ditolylbutadiene.

19. The composition of claim 1 wherein the metal complex is bis($\eta^5$-cyclopentadienyl)zirconium s-trans($\eta^4$-1,4-trans, trans-diphenyl-1,3-butadiene), bis(cyclopentadienyl) zirconium s-cis(2,3-dimethyl-1,3-butadiene), dimethylsilanediyl-bis((2-methyl-4-phenyl)-1-indenyl) zirconium s-trans($\eta^4$-1,4-trans-trans-diphenyl-1,3-butadiene), dimethylsilanediyl-bis((2-methyl-4-(1-naphthyl))-1-indenyl)zirconium s-trans($\eta^4$-1,4-trans-trans-diphenyl-1,3-butadiene), 1,2-ethanediyl-bis(2-methyl-4-(1-phenyl)-1-indenyl)zirconium s-trans($\eta^4$-1,4-trans-trans-diphenyl-1,3-butadiene), 1,2-ethanediyl-bis(2-methyl-4-(1-napthyl)-1-indenyl)-zirconium s-trans($\eta^4$-1,4-trans-trans-diphenyl-1,3-butadiene), [1,2-ethanediylbis(1-indenyl)] zirconium s-trans($\eta^4$-trans,trans-1,4-diphenyl-1,3-butadiene), [1,2-ethanediylbis(1-tetrahydroindenyl)]-zirconium s-trans($\eta^4$-trans,trans-1,4-diphenyl-1,3-butadiene), [1,2-ethanediylbis(1-indenyl)]hafnium s-trans ($\eta^4$-trans,trans-1,4-diphenyl-1,3-butadiene), or [2,2-propanediyl(9-fluorenyl)-(cyclopentadienyl)]-zirconium (trans,trans-1,4-diphenyl-1,3-butadiene).

20. The composition of claim 1 wherein the metal complex has the formula:

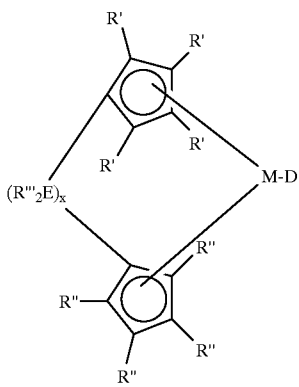

wherein:

M is titanium, zirconium or hafnium in the +2 or +4 formal oxidation state;

R' and R" in each occurrence are independently selected from the group consisting of hydrogen, hydrocarbyl, silyl, germyl, cyano, halo and combinations thereof, or adjacent R' groups or adjacent R" groups together form a divalent derivative thereby forming a fused ring;

E is silicon or carbon;

x is an integer from 1 to 8;

R'" is selected from the group consisting of hydrogen, methyl, benzyl, tert-butyl and phenyl; and D is a conjugated diene of 5 to 40 carbon atoms.

21. The composition of claim 20 wherein the metal complex is an ansa rac-metal complex.

* * * * *

UNITED STATES PATENT AND TRADEMARK OFFICE
CERTIFICATE OF CORRECTION

PATENT NO. : 5,972,822
DATED : October 26, 1999
INVENTOR(S) : Francis J. Timmers, et al It is certified that error appears in the above-indentified patent and that said Letters Patent is hereby corrected as shown below:

Title page, column 1, line 1, "BISCYCLOPENTADIENYLDIENE" should correctly read – BISCYCLOPENTADIENYL DIENE--.

Column 35, claim 3, line 47, "propanediylzirconium" should correctly read --zirconium--.

Column 36, claim 6, line 9, "claim 1" should correctly read --claim 4--.

Column 36, claim 17, formula, delete the formula and insert the following formula:

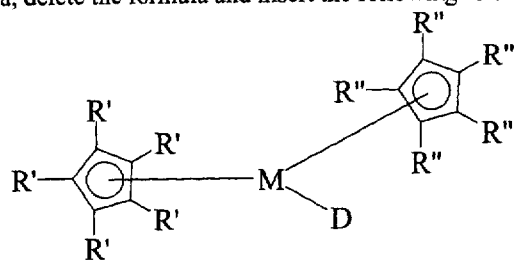

Column 36, claim 17, line 63, "a $C_{1-10}$" should correctly read --a terminally $C_{1-10}$--.

Signed and Sealed this

Twentieth Day of March, 2001

*Attest:*

NICHOLAS P. GODICI

*Attesting Officer*     *Acting Director of the United States Patent and Trademark Office*